United States Patent
Granados et al.

(10) Patent No.: US 6,187,558 B1
(45) Date of Patent: Feb. 13, 2001

(54) INVERTEBRATE INTESTINAL MUCIN CDNA AND RELATED PRODUCTS AND METHODS

(75) Inventors: Robert R. Granados; Ping Wang, both of Ithaca, NY (US)

(73) Assignee: Boyce Thompson Institute for Plant Research, Inc., Ithaca, NY (US)

( * ) Notice: Under 35 U.S.C. 154(b), the term of this patent shall be extended for 0 days.

(21) Appl. No.: 09/103,429

(22) Filed: Jun. 24, 1998

(51) Int. Cl.$^7$ ............................... C12P 21/06; C12N 1/20; C12N 15/00; C12N 5/00; C07H 21/04

(52) U.S. Cl. .................. 435/69.1; 435/252.3; 435/320.1; 435/325; 536/23.5

(58) Field of Search ................................ 536/23.1, 23.5; 530/350, 395; 435/69.1, 320.1, 252.3

(56) References Cited

FOREIGN PATENT DOCUMENTS

| | | | |
|---|---|---|---|
| 0 293 249 | 11/1988 | (EP) . | |
| WO 92/13075 | * 8/1992 | (WO) | ................................... 530/350 |
| WO 96/00783 | 1/1996 | (WO) . | |

OTHER PUBLICATIONS

Smith, Matthew D., Antibody Production in Plants, 1996, Biotechnology Advances, vol. 14, No. 3, pp. 267–281.

Adang, M. J. and Spence, K. D. (1983) Permeability of the peritrophic membrane of the Douglas fir tussock moth (*Oroyia pseudotsugatq*). Comparative Biochemical Physiology 75, 233–238.

Barbehenn, R. V. and Martin, N. M. (1995) Peritrophic envelope permeability in herbivorous insects. Journal of Insect Physiology 41, 303–311.

Begon, M.; Daud, K.B.H.; Young, P. and Howells, R.E. (1993) The invasion and replication of a granulosis virus in the indian meal moth *Plodia interpunctella*: an electron microscope study. Journal of Invertebrate Pathology 61(3), 281–295.

Brandt, C. R., Adang, M. J. and Spence, K. D. (1978) The peritrophic membrane: ultrastructural analysis and function as a mechanical barrier to microbial infection in *Orgyia pseudotsugata*. Journal of Invertebrate Pathology 32, 12–24.

Corsaro, B. G., Gijzen, M., Wang, P. and Granados, R. R. (1993) Baculovirus enhancing proteins as determinants of viral pathogenesis. In "Parasites and Pathogens of Insects Volume 2.—Pathogens", pp. 127–145. Academic Press, Inc., New York.

Derksen, A.C.G. and Granados, R. R. (1988) Alteration of a lepidopteran peritrophic membrane by baculoviruses and enhancement of viral infectivity. Virology 167, 242–150.

Faulkner, P.; Kuzio, J.; Williams, G. V. and Wilson, J.A. (1997) Analysis of p74, a PDV envelope protein of *Autographa californica* nucleoplyhedrosisvirus required for occlusion body infectivity. Journal of General Virology 78, 3091–3100.

Gallo, L. G., Corsaro, B. G., Hughes, P. R. and Granados, R. R. (1991) In vivo enhancement of baculovirus infection by the viral enhancing factor of the granulosis virus of the cabbage looper, *Trichoplusia ni* (Lepidoptera: Noctuidae) journal o–f Invertebrate Pathology 58, 203–210.

Gijzen, M.; Roelvink, P. and Granados, R. (1995) Characterization of viral enhancing activity from *Trichoplusia nj* granulosis virus. Journal of Invertebrate Pathology 65(3), 289–294.

Hawtin, R.E.; Zarkowska, T.; Arnold, K.; Thomas, C.j.; Gooday, G.W.; King, L.A.; Kuzio, J.A. and Possee, R.D. (1997) Liquefaction of *Autographa californica* nucleopolyhedrovirus–infected insects is dependent on the integrity of virus–encoded chitinase and cathespin genes. Virology 238(2), 243–253.

Hughes, P.R., van Beek, N.A.M. and Wood, H.A. (1986) A modified droplet feeding method for rapid assay of *Bacillus thruingiensis* and baculoviruses in Noctuid larvae. Journal of Invertebrate Pathology 48, 187–192.

Lehane, M. J. (1997) Peritrophic matrix structure and function. Annual Review of Entomology 42, 525–550.

Lepore, L. S., Roelvink, P. R. and Granados, R. R. (1996) Enhancin, the granulosis virus protein that facilitates nucleopolyhedrosis virus (NPV) infections, is a metalloprotease. Journal of Invertebrate Pathology 68, 131–140.

Primary Examiner—Scott D. Priebe
Assistant Examiner—Richard Schnizer
(74) Attorney, Agent, or Firm—Brown, Pinnisi & Michaels, P.C.

(57) ABSTRACT

The invention represents the disclosure of a novel insect intestinal mucin comprising two nearly identical isoforms, IIM14 and IIM22 respectively. These isoforms of the IIM protein have been identified and cloned using *T. ni* larva. The cDNA and amino acid sequences have been determined and are disclosed. Both IIM isoforms have an approximate molecular mass of 400 kDa. These sequences once disclosed are useful for the production of transgenic or recombinant vectors including viral, microorganism cell, plant, or animals, wherein the virus, microorganism, cell, plant, or animal is the product of an insertion of a gene expression vector including a DNA that encodes an IIM protein sequence. Thereafter the engineered host of the IIM DNA sequence is capable of expressing said IIM protein in a functional form. Also useful is a purified and isolated recombinant DNA sequence comprising a DNA sequence that codes for an IIM protein. The recombinant DNA sequence used can be a cDNA sequence for either IIM isoform IIM14 or IIM22, SEQ. ID.'s No. 1; and 3 respectively. The current invention also provides for the use of the purified amino acid sequences of IIM isoforms IIM14 or IIM22, SEQ. ID.'s 2 or 4 respectively. With this knowledge of the proteinaceous components of the PM, and particularly the mucin-like proteins it will be possible to enhance the effectiveness of bio-engineered pesticides, recombinant viral vectors, enhance the defenses of transgenic plants, or protect insect vectors susceptible to attack by organisms utilizing enhancin or enhancin-like enzymes.

8 Claims, 3 Drawing Sheets

OTHER PUBLICATIONS

Figure 1:
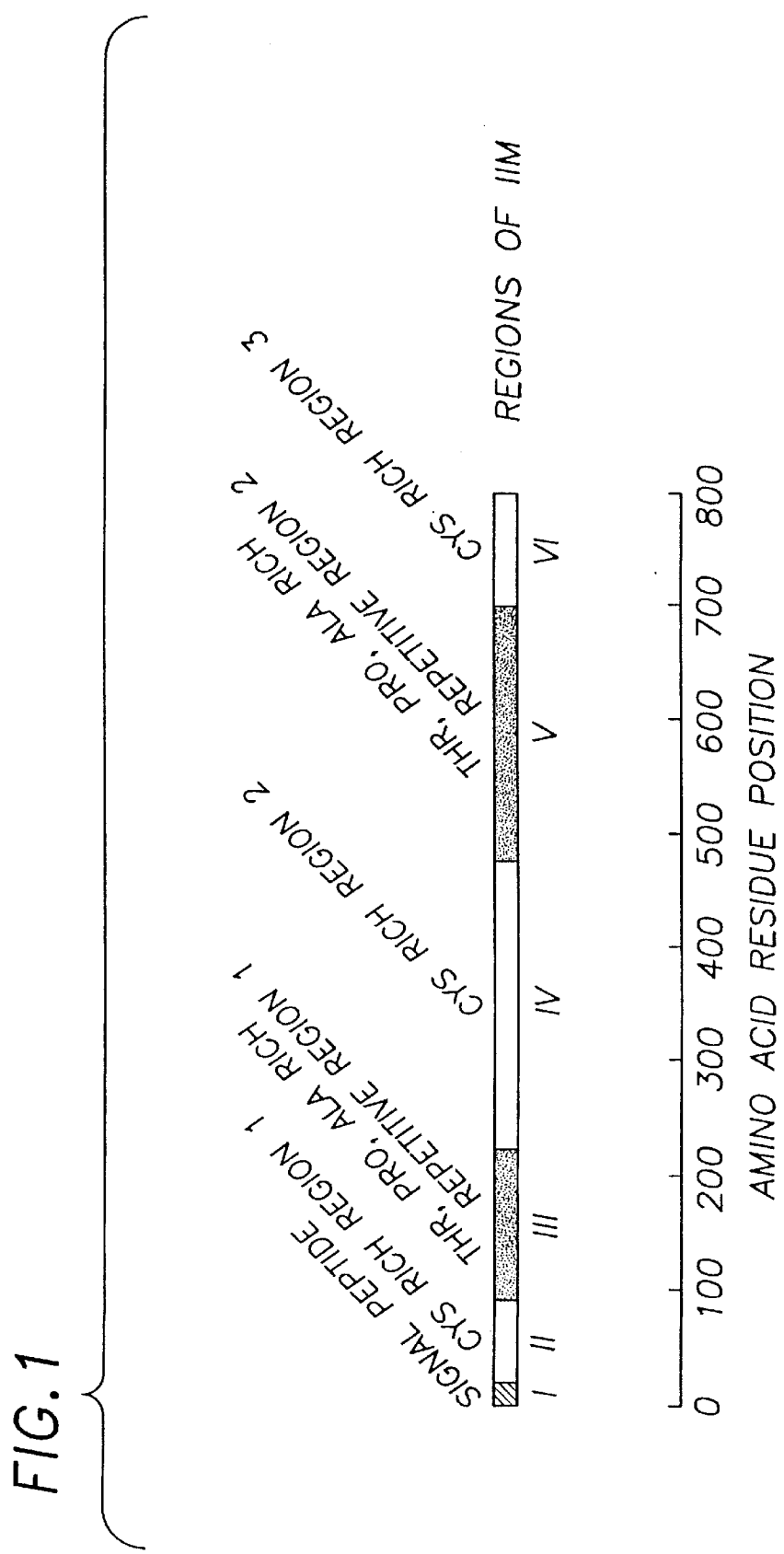

Miller, N. and Lehane, M. J. (1990) In vitro perfusion studies on the peritrophic membrane of the tsetse fly *Glossina moristans moristans* (Diptera, Glossinidae). *Journal of Insect Physiology* 36, 813–8128.

Miller, N. and Lehane, M. J. (1993) Ionic environment and the permeability properties of the peritrophic membrane of *Glossina moristans moristans, Journal of Insect Physiology* 39, 139–144.

Peters, W. and Wiese, B. (1986) Permeability of the peritrophic membranes of some Diptera to labeled dextrans. *Journal of Insect Physiology.* 32, 43–50.

Richards, A. G. and Richards, P. A. (1977) The peritrophic membranes of insects. *Annual Review of Entomology* 22, 219–240.

Sakurada, M.; Morgavi, D.P.; Komatani, K.; Tomita, Y. and Onodera, R. (1996) Purification and characteristics of cytosolic chitinase from *Piromyces communis* OTS1. *FEMS Microbiology Letters.* 137(1), 75–78.

Santos, C. D. and Terra, W. R. (1986) Distribution and characterization of oligomeric digestive enzymes from *Erinnyis ello* larvae and inferences concerning secretory mechanisms and the permeability of the peritrophic membrane. *Insect Biochemistry* 16, 691–700.

Spence, K. D. and Kawata, M. Y. (1993) Permeability characteristics of the peritrophic membranes of *Manduca sexta* larvae *journal of Insect* Physiology, 39, 785–790.

Tanada, H. (1985) A synopsis of studies on the synergistic property of an insect baculovirus: a tribute to Edward A. Steinhaus. *journal of Invertebrate* Pathology 45, 125–138.

Tellem, R. (1996) The peritrophic matrix. In "The Insect Midgut", (M. J. Lehane and P. F. Billingsley, Eds.), Chapman and Hall, London.

Wang, P. and Granados, R.R. (1996a) An intestinal mucin is the traget substrate for a baculovirus enhancin. Proceedings of the National Academy of Science, USA 94, 6977–6982.

Wang, P. and Granados, R. R. (1997b) Molecular cloning and sequencing of a novel invertebrate intestinal mucin Cdna. Journal of Biological Chemistry 272,16663–16669.

Wang, P. and Granados, R. R. (1998) Observations on the presence of the peritrophic membrane in larval *Trichoplusia m,* and its role in limiting baculovirus infection. Journal of Invertebrate Pathology, 72, pp 57–62.

Wang, P. Hammer, D. A. and Granados, R. R. (1994) Interaction of enhancin, a viral encoded protein, from the granulosis virus of *Tricoplusia ni* with the midgut epithelium and peritrophic membrane of four lepidopteran insects. Journal of General Virology 75, 1961–1967.

Wolfersberger, M. G., Spaeth, D. D. and Dow, J. A. T. (1986) Permeability of the peritrophic membrane of tobacco hornworm larval midgut. American Zoologist 26, 76A.

Zimmerman, D. and Mehlan, D. (1976). Water transport across peritrophic membranes of *Calliphora erythrocephala*—VII. Comparative Biochemistry and Physiology 55, 119–126.

* cited by examiner

INVERTEBRATE INTESTINAL MUCIN CDNA AND RELATED PRODUCTS AND METHODS

FIELD OF THE INVENTION

The invention pertains to the field of proteins associated with the peritrophic membranes of insects. More particularly, the invention pertains to a novel invertebrate intestinal mucin cDNA and related products and methods.

BACKGROUND OF THE INVENTION

Vertebrate epithelial organs are covered, throughout the body, with a mucus lining, which serves as a selective physical barrier between extracellular contents and the epithelial cell surface. The mucus lining, especially in the gastrointestinal tract, is highly resistant to various digestive enzymes and provides protection and lubrication for the underlying cells. The protective functions of the mucosal layer are largely dependent upon heavily glycosylated proteins known as mucins. Mucins play an active role in preventing bacterial, viral, and other pathogens from interacting with vertebrate intestinal epithelia.

Mucins are highly O-glycosylated proteins. Carbohydrate moieties on mucins commonly account for more than 50% of the protein by weight. The biochemistry and molecular biology of mucins from vertebrates has been broadly investigated, with human epithelial mucins being the most extensively studied. Several mucins from humans and other vertebrates have been completely or partially sequenced, and this has contributed to a greater understanding of their structure and function. Full cDNA sequences for human mucin MUC1, MUC2, and MUC7, have been obtained. In addition, mucins from other vertebrates, including mouse MUC-1, rat ascites sialo-glycoprotein-1, canine tracheobronchial mucin, bovine submaxillary mucin-like protein, and frog IIM-A.1, have also been fully sequenced by cDNA cloning.

Studies on invertebrate mucins are very limited in comparison with vertebrate mucins. *Drosophila melanogaster* "glue proteins" from salivary glands have structural characteristics of mucin-like proteins, which have been sequenced but whose function has not been fully determined. Mucin-like proteins have also been reported in protozoans. A secretory mucin involved in maintaining the cohesiveness of a clutch of a squid egg-mass formation was identified from that animal's nidamental gland. A glycoprotein from *Drosophila melanogaster* cultured cells was reported to be a mucin-like protein. Recently, a membrane-associated mucin from the hemocytes of *Drosophila melanogaster* was identified, and a cDNA for the mucin was subsequently cloned. However, to date, there have been no reports on mucins identified from invertebrate digestive tracts.

Part of the reason for this may be that insects do not possess a mucus layer lining the digestive tract and/or other epithelial cells, as do vertebrates. The digestive tract in insects is commonly lined with an invertebrate-unique structure, the peritrophic membrane (PM). PMs are non-cellular matrices composed primarily of chitin, protein, and glycoproteins. PMs demonstrate a protective function similar to the mucus layer in vertebrates (e.g. a selective barrier protecting the digestive tract from physical damages and microbial infections).

Although there are few studies on the interaction between microbial pathogens and PMs, these structures are proposed to serve as a physical barrier to invasion or infection by pathogenic microorganisms. The chitin component of PMs is normally present as a network of chitin fibrils in which proteins and glycoproteins are present. The chitin can be a potential target substrate for intestinal pathogens. This was demonstrated through the degradation of chitin in the PM by a pathogen-encoded chitinase allowing an avian malaria parasite to overcome its mosquito vector intestinal PM barrier and infect the vector itself.

Proteins are the major PM component; however, their functions in the PM are unknown. Studies on the PM proteins are limited to analyses of the amino acid composition of total PM proteins and PM protein profiles as determined by electrophoresis. The only PM protein characterized to date, peritrophin-44, was isolated from *Lucille cuprina* larvae, but its biological function is unclear. To date, studies on the interaction of PM proteins with microbial pathogens are limited to the effect of a baculovirus enhancin on lepidopteran PM proteins.

Previous studies have demonstrated that a *Trichoplusia ni* granulosis virus (TnGV) encodes an enhancin protein, a viral enhancing protein, that was identified as a metalloprotease. Enhancin degrades high molecular weight PM proteins in vivo and in vitro. In addition, the protein degradation initiated by these enhancins is correlated with the disruption of the structural integrity of the PM thereby "enhancing" viral infection. It was recently demonstrated that enhancin could degrade high molecular weight PM proteins from several lepidopterous species; however, the chemical nature and function of these proteins in baculovirus pathogenesis were previously unknown.

With a more complete knowledge of the proteinaceous components of the PM, and particularly the mucin-like proteins it will be possible to use that information to enhance the effectiveness of bio-engineered pesticides, recombinant viral vectors, enhance the defenses of transgenic plants, or protect insect vectors susceptible to attack by organisms utilizing enhancin or enhancin-like enzymes.

SUMMARY OF THE INVENTION

Briefly stated the current invention represents the disclosure of a novel intestinal insect mucin comprising two nearly identical isoforms, IIM14 and IIM22 respectively. This IIM protein has been identified and cloned from *T. ni* larva. Its cDNA and amino acid sequences have been determined and are disclosed. The IIM isoforms have an approximate molecular mass of 400 kDa. These sequences once disclosed are useful for the production of transgenic or recombinant vectors including viral, microorganism, cell, plant, or animals, wherein the virus, microorganism, cell, plant, or animal is the product of an insertion of a gene expression vector including a DNA that encodes an IIM protein sequence. Thereafter the engineered host of the IIM DNA sequence is capable of expressing said IIM protein in a functional form. One easily used host is the bacteria is *Escherichia coli*.

Also useful is a purified and isolated recombinant DNA sequence comprising a DNA sequence that codes for an IIM protein. The recombinant DNA sequence used can be a cDNA sequence for either IIM isoform IIM14 or IIM22, SEQ. ID.'s No. 1; and 3 respectively. The current invention also provides for the use of the purified amino acid sequences of IIM isoforms IIM14 or IIM22, SEQ. ID.'s 2 or 4 respectively.

With the cloned IIM sequence it is possible to prepare an IIM protein or peptide by transforming a host cell with an expresssion vector comprising a promoter operatively linked to a nucleotide sequence which codes for a fusion protein wherein said fusion protein comprises a first protein or peptide fused directly or indirectly with a transfer molecule said first protein or peptide being a predetermined protein or peptide of a *Trichoplusia ni* IIM protein. Then culturing the host cell under conditions such that the fusion protein is expressed in recoverable quantity. When harvesting the protein or peptide the cells must be collected, isolated, lysed, and the resulting cytosol purified for the created fusion protein.

A gene expression vector containing a recombinant DNA sequence encoding a *Trichoplusia ni* IIM protein sequence can also be constructed with this technology. This is accomplished through the use of a recombinant plasmid adapted for insertion into and transformation of bacteria or transgenic plants such that these hosts can express either the IIM protein or antibodies useful in fighting off plant pathogens. If it is not desirable to transform an expression vector with the entire IIM sequence then important peptide fragments or functional domains of the IIM protein or its isoforms can individually be transfected into expression vectors.

BRIEF DESCRIPTION OF THE DRAWING

FIG. 1 shows a schematic structure of the IIM protein.

FIG. 2 shows permeability characteristics of ligated midgut from larvae fed diet containing either IIM-IgG, normal serum IgG, or PBS. An intact, ligated midgut PBS–No Portal=PM not exposed) showed low passage of FITC-dextran across midgut wall.

FIG. 3 shows permeability characteristics of ligated midgut. Larvae were fed diets containing either IgG isolated from normal or anti-IIM serum or PBS. Each treatment and control are replicated.

DESCRIPTION OF THE PREFERRED EMBODIMENT

The following detailed description describes the methods used to discover and sequence a novel invertebrate intestinal mucin (IIM), isolate cDNAs encoding the isoforms of this novel mucin IIM14 and IIM22, and determine the role of this mucin in the function of the peritrophic membrane during infection by a pathogenic viral organism.

Isolation and Analysis of A Novel Invertebrate Intestinal Mucin

PMs have long been proposed as selective physical barriers in invertebrate intestines. The primary components of PMs include chitin protein and glycoprotein, but only one PM protein has been isolated and characterized thus far. PMs in invertebrates is analogous to vertebrate intestinal mucosal components that are secreted by epithelial cells. These vertebrate mucus secretions are composed primarily of one major constituent, intestinal mucin. Intestinal mucins from humans have been broadly studied, and the major human intestinal mucin (MUC2) was fully sequenced. Prior to the present invention, no intestinal mucin had been identified from invertebrates.

The present invention shows a novel invertebrate intestinal mucin (IIM). The novel mucin was first isolated from an insect larvae, *Trichoplusia ni* larvae from a laboratory colony reared on a high wheat-germ diet. Midgut PM was dissected from mid-fifth instar *Trichoplusia ni* larvae, thoroughly rinsed with de-ionized water, and stored at −70° C. PM proteins were solubilized by boiling PMs in SDS/PAGE sample buffer, and then separated by SDS/PAGE electrophoresis The IIM protein, and its isoforms, disclosed herein is a new type of mucin that represents the first intestinal mucin identified from an invertebrate.

To prepare IIM for antiserum production, protein bands can be first visualized by staining the gel with 0.05% Coomassie blue R-250 in 40% methanol followed by de-staining with de-ionized water; this procedure can be followed by excision of the IIM band from the eletrophoresis gel. After equilibration in a SDS/PAGE running buffer, the IIM in the gel slice is electroeluted, and the preparation is purified and concentrated and re-suspended in PBS by ultrafiltration using a centriprep-30 concentrator (Amicon).

For general biochemical analyses, PM protein bands on the SDS/PAGE gel can be initially visualized by copper staining, which facilitates the excision of the IIM band. IIM from this gel slice is also electroeluted after copper ions are removed by washing the gel slice several times in 0.2 M EDTA. Subsequently, the eluted protein preparation is desalted by ultrafiltration.

To isolate and purify the IIM protein (e.g. including both isoforms) for amino acid composition analysis, the sodium phosphate-buffered SDS/PAGE system is used. The gel is stained with copper chloride after equilibration of the gel in 0.375 M Tris-HCl (pH 8.8) with 0.1% SDS. The IIM band is excised and the IIM is recovered by electroelution as described above; the preparation is further desalted by extensive dialysis against de-ionized water and then lyophilized.

IIM from *Trichoplusia ni* PMs is a 400-kDa protein on 3.5% SDS/PAGE gels. The association of the IIM with PMs is stable over a wide range of pH, in the presence of non-ionic and ionic detergents, and in the presence of protein denaturing reagents. Therefore, very little, or no IIM was present in the supernatants from these treatments. IIM, the predominant PM protein, could be released from the PM by a combination of 2% SDS plus 5 mM DTT, confirming that it was strongly associated with the chitin-containing PM matrix. The IIM was not extracted from the PM by boiling in 2% SDS for 10 min unless a reducing agent was included, demonstrating the presence of intermolecular disulfide bonding in native IIM Amino acid composition analysis of IIM, indicated that IIM was rich in threonine (18.7%) proline (16.9%), and alanine (15.9%). These three amino acids accounted for 51.5% of the total amino acid residues in the protein, while aromatic amino acids accounted for less than 5% of the amino acid residues in the protein, and may account for the ability of IIM to by strongly associated to the invertebrate PM chitin fibrils. The IIM amino acid composition profile resembles that of a typical vertebrate mucin that is commonly rich in threonine, serine, proline, alanine, and glycine, and rare in aromatic amino acids.

Quantification of the protein and carbohydrate content of IIM indicated that it was highly glycosylated. Carbohydrate content on IIM accounted for 56% of the total IIM mass, with protein accounting for 44%. Terminal mannose residues and galactose β(1-3) N-acetylgalactosamine were detected on IIM by the specific binding of peanut agglutinin and *Galanthus nivalis* agglutinin (GNA). The lectin binding assays using IIM samples pretreated with either O-glycosidase or N-glycosidase showed no binding or significantly reduced binding of the lectins, confirming the positive recognition of *G. nivalis* agglutinin and peanut agglutinin to IIM. These results demonstrated that IIM has both N-glycosylation and O-glycosylation, since terminal mannose is present in N-linked carbohydrate moieties and galactose β(1-3) N-acetylgalactosamine is one type of O-linked carbohydrate moiety found in glycoproteins. In addition, removal of the disaccharide, galactose β(1-3) N-acetylgalactosamine by O-glycosidase treatment, resulted in significant reduction (approx. 100 kDa) in the molecular weight of the IIM, further confirming the heavy O-glycosylation on IIM.

The experiments conducted demonstrated the highly protease-resistant nature of the isolated IIM isoforms. The stability of the IIM when exposed to degestive enzymes for long periods is aided by the O-linked carbohydrate moieties found in associated glycoproteins. The IIM was highly resistant to endogenous digestive even after a sixteen hour incubation, no degradation of IIM in PMs was observed. However, in the presence of O-glycosidase, IIM was quickly degraded. Control treatments using PMs with inactivated or inhibited endogenous midgut proteases, confirmed that the degradation of IIM in the presence of O-glycosidase was a result of hydrolysis by endogenous digestive proteases, following removal of the protective carbohydrate moiety, galactose β(1-3) N-acetylgalactosamine.

The isolated and sequenced IIM from *Trichoplusia ni* PM resembles mammalian secretory mucins in several characteristics, including high O-glycosylation, possible intermolecular cross-linking disulfide bonds, high concentrations of threonine alanine and proline, and resistance to proteases. Selective removal of galactose β(1-3) N-acetylgalactosamine resulted in greatly increased susceptibility to proteolysis indicating that this O-Linked disaccharide plays an important role in protecting the IIM protein from digestive degradation. Unlike vertebrate mucins, insect PM proteins are embedded in a chitin fibril network. The inability to extract the IIM from PMs with various detergents and extreme conditions in the absence of a reducing agent demonstrate that IIM is tightly associated with the chitin-rich PM matrix and that disulfide bonding is seemingly important for this association.

Isolation and Sequencing of A Novel Invertebrate Intestinal Mucin cDNA

The present invention teaches cloned and sequenced full-length cDNAs for IIM from *Trichoplusia ni*. IIM has a similar structural organization to human intestinal mucin, MUC2, and is expressed in midgut tissue. Sequence analysis indicates potential chitin binding domains that may interact with the chitin present within the PM.

A cDNA expression library was constructed from *Trichoplusia ni* midgut mRNA. Midgut epithelial tissues were dissected from early to mid-fifth instar *Trichoplusia ni* larvae in cold Rinaldini's solution. PMs with food contents and other attached tissues (i.e. fat bodies, trachea, and malphighian tubules) were quickly removed from the midgut epithelium. Isolated midgut epithelia were rinsed with cold Rinaldini's solution, quickly frozen in liquid nitrogen, and stored at −70° C. prior to use. Midgut mRNA was isolated using the RNeasy total RNA isolation kit and the Oligotex mRNA isolation kit Qiagen Inc., Chatsworth, Calif.), according to the manufacturer's specifications. The quality of mRNA was confirmed by Northern blot analysis, which showed no detectable degradation of mRNA after probing with B-tubulin DNA. The cDNA library was constructed from *Trichoplusia ni* midgut mRNA using the ZAP-cDNA Gigapack Cloning Kit (Stratagene, La Jolla, Calif.), following the manufacturer's instructions. cDNA was unidirectionally ligated into the Uni-ZAP XR vector (Stratagene, La Jolla, Calif.) between the EcoRI and XhoI sites and packaged with the Gigapack II Gold package extract. The resultant cDNA library was amplified once at 50,000 plaques/15-cm plate in XL1-Blue MRF' *E. coli* host cells.

The library has a complexity of 2.35×10$^6$ plaques, of which over 99.5% were recombinants. Screening of the cDNA expression library for IIM cDNA clones was conducted using an IIM-specific polyclonal antiserum in conjunction with the pico Blue Immunoscreening Kit (Stratagene, La Jolla, Calif.), according to the manufacturer's specifications. The first round of screening was performed at a high density (i.e. 50,000 plaques/15-cm plate). Positive plaques were selected and further purified by screening at a low plating density (i.e. 20–50 plaques/10-cm plate). From purified positive phages the pBluescript SK (−) phagemid (Stratagene, La Jolla, Calif.) was excised in vivo following the ZAP-cDNA Gigapack cloning kit protocol.

Screening of the library with the antiserum specific to IIM indicated that the mRNA for the IIM was abundant; 50 positive plaques were obtained from 50,000 plaques. Since only one in three plaques will be in the correct reading frame for protein expression, the frequency of IIM cDNA clones could be 1 in 333. From these 50 plaques, 20 positive plaques were further purified. From these 20 plaques, the pBluescript SK(−) phagemids were rescued by in vivo excision. Following restriction enzyme analysis to map the selected clones, two different full-length clones, pIIM14 and pIIM22, were chosen for sequencing.

Nested deletions from both orientations of the cDNA inserts were constructed using the Erase-a-Base System (Promega Corp., Madison, Wis.). Both strands of the cDNA were sequenced by automated cycle sequencing using T3 and T7 primers, complementary to the pBluescript SK(−) sequences flanking the cDNA inserts. DNA sequence analysis and a data base search were conducted using the DNAS-TAR software package (DNASTAR Inc., Madison, WD and BLAST data base search programs. Protein O-glycosylation sites were predicted following an O-GLYCBASE search.

The cDNAs from both pIIM14 and pIIM22 were full-length clones, encoding a protein of 788 and 807 amino acid residues, respectively. The nucleotide sequence of each is shown in SEQ. ID. NO. 1 & 3, respectively. The open reading frame in the cDNA from IIM14, was 57 base pairs shorter than in IIM22; otherwise, the open reading frames in these two clones were identical. IIM22 contains a putative polyadenylation signal consensus, AATAAA, located 331 base pairs downstream of the translation stop codon, TAA and 17 base pairs upstream of the poly(A). IIM14 contains a putative polyadenylation signal, AATTAA, located 15 base pairs upstream of the poly(A).

The deduced protein sequences from IIM14 and IIM22 showed a hydrophilicity profile characteristic of a signal sequence at the N terminus of protein sequences. The N-terminal amino acid sequence determined from purified IIM indicated that the cDNA clones encode a protein containing a signal peptide 25 amino acids long and confirmed that the cDNA clones code for the IIM. The amino acid composition of the deduced proteins from IIM14 and IIM22 were very similar to the composition of IIM isolated from *Trichoplusia ni* further confirming that the cDNA clones code for the IIM. Protein sequence data reveal that there are four potential N-glycosylation sites. This is in agreement with the biochemical analysis results which demonstrated that TIM has N-linked glycosylation. The amino acid sequence of IIM14 and IIM22 is shown in SEQ. ID. NO. 2 & 4 respectively.

Referring to FIG. 1, the overall IIM sequences can be divided into six distinct regions based upon their sequence features. FIG. 1 shows a schematic structure of the IIM protein. The amino acid composition of each region shows characteristics of a secreted epithelial mucin. Both the N-terminal and C-terminal domains, are rich in cysteine, which accounts for 8.2 and 7.8% of the total amino acid residues, respectively. Region III is rich in threonine, proline, and alanine (49.2, 16.2, and 21.5%, respectively) and contains two types of tandem repeats, TTTQAPT and AATTP, which are typical features for a mucin (6, 32). Region IV is similar to regions II and VI and contains 9.0% cysteine residues. Region V is another threonine-, Proline-, and alanine-rich section, containing a repetitive sequence, TAAP This region differed between IIM14 and IIM22 in sequence length, but the sequence features of the IIM protein isomers, and their respective cDNA clones were similar. This region (V), contains 25 TAAP repeats in IIM22.

Northern blot analysis of *Trichoplusia ni* midgut RNA with a probe made from IIM22 showed a single band with a molecular size of 3.1 kilobase pairs, indicating that there was no similar polydispersity in IIM transcription, as is found in mammalian mucin transcripts.

Biochemical analysis has shown that IIM from *Trichoplusia ni* midgut peritrophic membranes is a novel invertebrate intestinal mucin. The cDNA sequence presented here confirms the identity of this secreted invertebrate intestinal mucin. The overall structural organization of IIM is similar to human intestinal mucin, MUC2. which can be described as follows: (a) as a secreted mucin, the IIM contains a 25-amino acid signal peptide at the N terminus (region 1); (b) relative to MUC2, which has two different tandem repeat domains interspersed by a cysteine-rich region that distinguishes MUC2 from other mucins, IIM also contains two threonine-rich tandem repeat regions (regions III and V) where potential O-glycosylation sites are located; and (c) the two tandem repeat regions are flanked by cysteine-rich regions (regions II, IV, and VI) (FIG. 1).

In comparison with MUC2, which contains more than 5100 amino acid residues, the apoprotein in IIM is relatively small. The mature IIM isoforms contain either 763 or 782 amino acid residues. Prediction of O-glycosylation using the O-GLYCBASE search program indicated that 127 of the 147 threonine residues and 5 of the 23 serine residues in IIM22 (excluding the signal peptide) were potential O-glycosylation sites. In regions III and V, all threonine residues, except the two at the boundaries of region III (at position 99) and region V (at position 486), were potential O-glycosylation sites. There is only one threonine in the non-tandem repeat domains (at position 314) marginally predicted as a potential O-glycosylation site. A PROSITE data base search using DNASTAR demonstrated four tentative N-glycosylation sites. All four sites were located within region V.

Regions III and V contain high levels of threonine, alanine, and proline, and do not contain any aromatic or sulfur-containing amino acids, which is similar to the corresponding domains in MUC2. IIM contains multiple repeating units. These repeating units are short compared with those found in mammalian mucins. Region III contains two tandem repeating sequences, TTTQAPT and AATTP, throughout the whole region. Region V contains an even shorter repeating unit, TAAP. The repeating units in this region are dispersed at four potential N-glycosylation sites and several other locations. Sequences TTVT(V/S)PP and TTAVPEI occur frequently in the disrupted locations in region V. The repeating sequences in IIM did not exhibit similarity to any known repeating sequences from other mucins.

The difference between cDNAs IIM14 and IIM22 is in region V. In this region, IIM14 contains 19 fewer amino acids than IIM22, which could be due to genetic polymorphism, as reported for human and other vertebrate mucin genes. Both IIM cDNAs contain G+C-rich repeated sequence units in region III and V. These G+C-rich repeated sequences (with X-like sequence features), could be responsible for the evolution of genetic polymorphisms. This difference between IIM14 and IIM22 could also be the result of alternative splicing during RNA processing. Such a phenomenon has been observed in mucin gene expression. The AG at position 2005 and 2006 in IIM22 could potentially serve as a 3'-splicing site, which would lead to a mRNA corresponding to IIM14.

The protein sequence features of the IIM isoforms are in agreement with the data from the biochemical analysis of IIM. The presence of N-glycosylation motifs and mucin-characteristic threonine-rich tandem repeats in the IIM sequence confirmed the presence of N-glycosylation and extensive O-glycosylation of IIM, previously analyzed by carbohydrate-specific lectin binding and specific glycosidase analyses.

Cysteine-rich domains are common in mucins and have been demonstrated to cause oligomerization of mucins by disulfide bonding. These cysteine-rich regions might also contain globular structures with intramolecular disulfide bonds. These protein regions could become exposed once the disulfide bonds are reduced. Disulfide bonds in the non-heavily O-glycosylated regions of IIM are involved in maintaining a digestive protease-resistant structure. However, protein sequence analysis did not show significant sequence similarity between the cysteine-rich regions in IIM and the cysteine-rich regions from MUC2, or other mammalian mucins. This is not surprising, since insects are phylogenetically very distant from mammals and since IIM is a constituent of a unique invertebrate chitin-containing structure.

IIM is tightly associated with the PM, and is a major structural constituent of the PM. These results indicate that IIM may have a high affinity to the chitinous fibril network of PMs. By computer-assisted sequence analysis, a protein fragment in region IV was aligned to two chitin binding domains in chitinases from a yeast, *Saccharomyces cerevisiae,* and a fungus, *Rhizopus oligosporus.* In addition to region IV, sequences in regions II and VI also show a certain degree of similarity to the chitin binding domains described above; however, the levels of similarity were lower than that found in region IV. In a recent report, a non-mucin insect PM protein from *Lucilia cuprina,* peritrophin-44, showed binding capability to chitin, but it did not show significant sequence similarity to known chitin binding sequences. However, the cysteine-rich domains with peritrophin-44 shared the same structural feature, a six-cysteine-containing sequence present in cysteine-rich domains in chitinases.

Surprisingly, the sequence features of IIM in the cysteine-rich regions are similar to what Elvin et al. proposed for peritrophin-44. Almost all sequences in regions II, IV, and VI are composed of such a six-cysteine consensus. This result supports the conclusion that IIM may tightly bind to the chitin network of PM in the non-glycosylated cysteine-rich regions. The strong binding of IIM to chitin could be a very important factor for the formation of PMs in invertebrates and aid in the stability of the chitin network. Based on the structural characteristics of IIM and the strong binding associated with IIM and chitin, it is likely that the chitin fibrils in PMs are protected from enzymatic degradation by IIM. Considering the biochemical properties of IIM and the putative chitin binding sequences in non-glycosylated regions in IIM the IIM protein backbone is protected from degradation in the hydrolytic enzyme-rich midgut environment by two different mechanisms: (a) the densely O-glycosylated regions (regions III and V) are protected by oligosaccharide moieties; and (b) the cysteine-rich non-glycosylated or less glycosylated regions (regions II, IV, and VI) are protected by disulfide covalent bonding forming a "buried" structure or by the protein binding to chitin in the PM. The mucin nature and chitin binding capability of IIM can explain the high resistance of IIM to midgut digestive enzymes and the protective functions of PMs in invertebrates, especially in insects, Any reagents with the potential effect of damaging IIM, such as baculovirus enhancins or reducing agents, will result in the destruction or attenuation of the protective role of the PM against parasites and other microorganisms.

Localization of Expression of the Mucin in the Peritrophic Membrane

By immunolocalization in tissue sections, it was determined that IIM is expressed in midgut tissues.

The IIM from *Trichoplusia ni* larvae was localized by immunocytochemistry with the antiserum to IIM. An antiserum to IIM was generated by immunizing a Flemish Giant/Chinchilla Cross rabbit with purified IIM from *Trichoplusia ni* PMs. Preimmune serum from the rabbit was collected and used as a control for immunodetection of IIM. Fourth instar *Trichoplusia ni* larvae were fixed in 4% paraformaldehyde overnight at 4° C. and embedded in paraffin. After tissue sectioning and de-waxing immunostaining was performed as follows: sections on glass slides were blocked for nonspecific staining with 3% bovine serum albumin in phosphate-buffered saline, followed by incubation with antiserum against IIM in phosphate-buffered saline containing 3% bovine serum albumin. After incubation with the first antiserum, the sections were washed with phosphate-buffered saline and incubated with a secondary antibody against rabbit IgG conjugated with colloidal gold (Sigma). Following secondary antibody incubation and subsequent washing, the sections were fixed with 2.5% glutaraldehyde. Immunogold staining was intensified by silver enhancement using the Silver Enhancer kit (Sigma). The immunostained sections were counterstained with hematozylin and eosin and examined by microscopy.

Microscopic observations showed that IIM was localized in the peritrophic membrane and in the area surrounding the midgut epithelial brush border. Observation at a high magnification demonstrated that IIM could be secreted from goblet cells of the midgut epithelium. Immunostaining with preimmune serum from the same rabbit used to generate the anti-IIM antiserum did not show any positive reaction. In addition to the midgut, positive staining was occasionally observed in malpighian tubules on the lumen side. To verify whether this occasional positive staining in malpighian tubules was specific to IIM and to test whether IIM was present in other tissues, a Western blot analysis of extracts from various tissues of *Trichoplusia ni* larvae using anti-IIM antiserum was conducted.

Tissues were isolated from fifth instar *Trichoplusia ni* larvae and rinsed with phosphate-buffered saline. The tissues were then homogenized and boiled in 0.0625 M Tris-HCI (pH 6.8) containing 2% SDS, 5% Beta-mercaptoethanol, and 10% glycerol. Undissolved materials were removed by centrifugation. Protein concentrations in the supernatants were estimated using the Bradford protein assay. One microgram of protein from each tissue extract, except for the PM extract, for which 0.04 µg of protein was used, was loaded onto the gel. Proteins were separated by SDS-PAGE, followed by blotting onto Immobilon membrane (Millipore Corp., Bedford, Mass.), and probed with anti-IIM antiserum.

The Western blot analysis showed that IIM was primarily present in the non-cellular PM. A broad band at 200 kDa could also be detected in the PM extract when this sample was overloaded. This band is considered a degradation product of IIM by active midgut digestive enzymes, since the PM moved through the digestive tract. The midgut was the only tissue in which a significant amount of IIM was detected. Besides the IIM band, some lower molecular weight bands were also present in the midgut extract. These bands possibly were the IIM protein in the process of glycosylation but not yet fully glycosylated. The extract from malpighian tubules did not show any positive staining at the gel position for IIM. Some weak positive staining was detected in the extract from hemolymph with a major broad band between 66 and 97 kDa. Salivary gland, fat body, and epidermis extracts did not show any positive reaction to the anti-IIM antiserum. The bands detected in the malpighian tubules and hemolymph did not show the correct molecular weight corresponding to IM, and the reactivity to the anti-IIM serum was very low. Therefore, the proteins represented by these bands do not indicate the presence of IIM in tissues other than the PM.

Localization of IIM by immuno cytochemistry indicates that IIM is primarily expressed in the midgut tissue and is likely to be secreted by goblet cells. Interestingly, this is similar to the secretion of mucins by goblet cells in vertebrate intestinal epithelium.

Peritrophic Membrane Secretion Patterns of Invertebrate Intestinal Mucin

*Trichoplusia ni* PM first appears in larvae before feeding starts and is present along the entire length of the mesenteron. IIM plays a significant role in the formation and function of the peritrophic membrane. To ascertain the secretion patterns of IIM, PM structure and secretion patterns were examined in the anterior, middle and posterior regions of the mesenteron.

Third instar larvae were allowed to fed on diet up to 24 hours. Prior to dissection, larvae were placed in wax-filled Petri dishes, stretched and pinned through the head capsule and telson, using pins held with forceps. The larvae were then flooded with cold fixative (3.2% formaldehyde, 5% glutaraldehyde in 0.1 M Sorensen's phosphate buffer, pH 7.2 containing 3% sucrose) and dissected to remove the cuticle. The exposed alimentary canal was fixed for 2 hours at 4° C., washed in 0.1 M Sorensen's phosphate buffer containing 3% sucrose for 2 hours, post-fixed in 1% osmium tetroxide in 0.1 M sodium cacodylate buffer, washed in double distilled water (ddw), stained en bloc for 4 hours with 2% aqueous uranyl acetate (on ice), washed in cold ddw for 0.5 h, and then dehydrated in an ascending ethanol series from 50 to 100%. The specimens then were infiltrated with a 1:2 mixture of ethanol: Spurr's resin for 1 h, followed by a 1:1 mixture for 2 h, and lastly placed in 100% Spurr's resin overnight. The specimens in resin were embedded in molds and cured for 60° C. for 24 hours Other specimens also were embedded in LR White resin for immunocytochemical procedures. Dissections were performed as above except the fixative contained 4% paraformaldyde and 0.5% glutaraldehyde in 0.1 M phosphate buffer saline (PBS), pH 7.2. Freshly dissected alimentary canals were fixed in this solution overnight, incubated in 0.1 M ammonium chloride in PBS for 1 h, washed in PBS for 2 h, and dehydrated in ascending ethanol series from 50 to 100%. The specimens were resin infiltrated with a 1:1 LR White: ethanol mixture for 2 h, transferred to 100% resin with one change, and kept overnight to allow complete resin infiltration. The specimens in resin were loaded into gelatin capsules and allowed to polymerize at 50° C. overnight. Thick sections (0.5 $\mu$m) were cut using glass knives on Reichert Ultramicrotome. For transmission electron microscopy (TEM), thin sections were cut using a diamond knife and mounted on naked or formvar-coated nickel grids and observed on a Phillips EM 201 transmission electron microscope.

For Wheat Germ Agglutinin staining, thin sections were incubated for 1 hours at room temperature in blocking buffer [0.01 M PBS (pH 7.2) containing 1% cold water fish gelatin, 0.075% Tween 20, and 0.075% Triton X-100] and subsequently incubated in a 1:100 dilution of 20 nm gold-labeled WGA (20 $\mu$g/ml) (E-Y Laboratories, San Mateo, Calif.) in blocking buffer for 1 hour. After incubation, grids were washed with PBS, ddw and stained with uranyl acetate (UA) and lead citrate (PbC). Cytochemical controls consisted of addition of 1 part 10 mM chitotriose with 1 part WGA solution at twice the above concentration.

Invertebrate intestinal mucin (IIM) was localized in thin sections which were first blocked in blocking buffer then incubated in a 1:300 dilution of anti-IIM preparation for 1 hours. Sections were then washed in multiple changes of blocking buffer for 1 hours then incubated in 1:100 dilution of 20 nm gold conjugated goat anti-rabbit IgG (E-Y Laboratories, San Mateo, Calif.) for 1 h. Sections were then washed with blocking buffer, PBS, ddw and stained with UA and PbC. Cytochemical controls were first incubated in a 1:300 dilution of rabbit preimmune serum for 1 h, washed in PBS for 1 hours and incubated in secondary antibody as described above. Scanning electron microscopy (SEM) was performed on *Trichoplusia ni* larvae. The midgut and PM were dissected and placed in Karnovsky's fixative for 2 hours. The specimens were then dehydrated in an ascending ethanol series from 70 to 100%, critical point dried, fixed to aluminum stubs with silver paste, sputter coated with gold-palladium, and viewed in an AMR-100A scanning electron microscope.

PM was present along the entire length of the mesenteron. In the most anterior midgut region examined, PM appeared as a single thin structure located between the stomodeal valves and midgut epithelium. Slightly posterior to this region (about 2 mm) PM appeared slightly thicker. This slight increase in thickness may be the result of the association of fine thread-like material to the delaminated PM. In the middle region of the mesenteron, the morphology of the PM changed to a more robust structure composed of compact layers. Similar in appearance to PMs located in the middle portion of the mesenteron, PM in the posterior mesenteron (Oust adjacent to the proctadaeum) can be seen at lower magnifications partitioning dietary plant cell walls and microbes from the underlying midgut epithelium.

Observations taken from electron micrographs shows PM formation begins with the appearance of fine fibrous-like material within the brush border of the anterior mesenteron. These nascent PMs first appear in the upper third of the microvillar brush border as diffuse structures. Probing these regions with anti-IIM and WGA-gold, produce discrete lines of labeling confined to these fibrous-like structures. These staining patterns indicate IIM and chitin (or N-acetyl-D-glucosamine containing structures) to be present in the nascent PM. This same binding pattern can be seen at the tips of the microvillar brush border demonstrating that nascent PM moves apically for delamination into midgut lumen. These delaminated PMs have a fibrous appearance and bind both WGA-gold and anti-IIM. Scanning electron microscopy (SEM) of the anterior midgut region revealed a microvillar brush border inundated with various amounts of material. Interestingly, SEM apparently captured individual secretion events where PM was resting above cells. At higher magnifications, these newly delaminated PMs possessed fibrous-like material, which is mostly obscured by smooth matrix material. Finally, these individual secretion events coalesce form a large smooth and continues PM which now conceals the underlying midgut epithelium.

To determine when PM first appears within the midgut lumen, third instar and newly molted third instar larvae were examined for the presence of PM. Although PM was not found in the pharate stage, there was localization of anti-IIM within the brush border (data not shown). Examination of newly ecdysed larvae (which have just passed their exuviae across the telson) showed a well-developed PM within the middle part of the midgut. In these larvae, the anterior midgut showed the presence of diffuse material packed between the interstices of microvilli. This material labeled extensively with anti-IIM and was present in the gut lumen above newly secreted PM. Interestingly, there was an association of this diffuse material to delaminated PMs. Finally, the staining patterns of IIM were investigated through out the length of the mesenteron. Cells located in the anterior midgut possessed vesicles, which were extensively labeled with anti-IIM. In the posterior regions, anti-IIM localized to microvillar brush border to columnar epithelial cells adjacent to goblet cells. This same phenomenon was observed in the brush border of cells from the middle portion of the mesenteron.

At the entrance of the mesentron, the PM was observed as a thin structure sandwiched between the tips of the microvillar brush border and intima of the stomodeal valves. This delicate-looking membrane increased in thickness as is it moved in a posterior direction toward the proctodaeum. The delamination of PM from the microvillar brush border was only observed in the anterior mesenteron. No PM delamination events were seen in the middle or posterior mesenteron. Furthermore, sections representing the mid- and posterior mesenteron showed no discrete lines of labeling within the brush border when probed with anti-IIM or WGA-gold. This observation demonstrates that chitin and IIM do not aggregate to form nascent PM in regions past the anterior mesenteron. Within the anterior mesenteron, PM formation begins with the secretion of chitin and matrix material (IIM). These PM components appear to first aggregate within the upper part of the brush border to from a nascent PM. This is followed by delamination of PM into the midgut lumen. Even though PM delamination events appears to be restricted to the anterior mesenteron, there is secretion of IIM from cells located in the middle and posterior midgut. In the middle and posterior mesenteron, the majority of anti-IIM localized to the brush border. Secretion of IIM through out the entire length of the mesenteron may account for the observed increase in PM thickness. Interestingly, IIM secretion was often localized to columnar epithelial cells directly adjacent to goblet cells.

Our observations that PM formation is restricted to the anterior part of the midgut is consistent with previous studies. In one study, the European corn borer (ECB, *Ostrinia nubilalis*) larval PM formation was found to be limited to the anterior mesenteron. In this region, ECB nascent PM was embedded within the brush border and stained with WGA-gold (indicating the presence of chitin containing structures). Even though the authors were able to determined an anterior site of chitin substructure assembly and delamination, they were unable to directly determine where protein matrix was synthesized and secreted. The current disclosure demonstrates that the midgut region is responsible for the secretion of protein matrix in *Trichoplusia ni* larvae. By probing the midgut for the major protein moiety IIM, it was determined that the chitin substructure and protein matrix (IIM) apparently are secreted together from cells located within the anterior part of the mesenteron. These results are consistent with the SEM observations which show fibrous linear structures (assumed to be chitin microfibrils) embedded in a proteinaceous matrix. Finally, another very interesting observation is the secretion of IIM through out the mesenteron. This whole midgut secretion phenomenon may provide additional amounts of matrix material to damaged PMs. This may in turn preclude microbes and rough dietary components access to the midgut epithelium.

The Role of the Mucin in the Function of the Peritrophic Membrane and Baculovirus Infection A baculovirus enhancin, which is encoded and carried by specific baculoviruses, has mucin-degrading activity both in vitro and in vivo. The in vivo degradation of IIM by enhancin was correlated with the enhancement of baculovirus infections in insects. These findings show that viruses have evolved a novel strategy to overcome intestinal mucinous barriers against microorganisms by utilizing a mucin-degrading enzyme.

Incubation of IIM with Tn enhancin showed that the enhancin had activity against IIM. To demonstrate proteolytic activity by TnGV enhancin against IIM, purified IIM was incubated with 1.25 $\mu$g/ml TnGV enhancin in 0.05 M Tris-HCl buffer (pH 7.5) containing a cocktail of protease inhibitors minus the metalloprotease inhibitor, EDTA at 37° C. for 3 hours or overnight. The degradation of IIM was examined by SDS/PAGE analysis. A parallel treatment of IIM without enhancin was included as a control. The degradation products of IIM displayed a banding pattern similar to that observed during incubation of intact PMs with enhancin. To confirm the metalloprotease nature of enhancin, IIM was incubated with TnGV enhancin in the presence of 10 mM EDTA. The addition of 10 mM EDTA to the incubation buffer blocked the digestion of the IIM and confirmed the metalloprotease nature of enhancin.

In vivo IIM degradation assays with *Trichoplusia ni* neonate larvae demonstrated that enhancin degraded IIM in the midgut of living insects and that the degree of degradation appeared to be dose-dependent. Two in vivo assays were developed to include neonate and fifth instar *Trichoplusia ni* larvae, based on the methods employed to determine the efficacy of an enhancin on virus infections. The in vivo neonate IIM assay and a concomitant virus bioassay were conducted by feeding *Trichoplusia ni* neonate larvae with inoculum droplets containing $10^5$ occlusion bodies/ml of AcMNPV, and varying doses of TnGV enhancin, as described by Wang et al. Following ingestion of the inoculum, 25 larvae from each treatment were transferred onto artificial diet, incubated at 28° C. for 90 mnin, and collected for Western blot analysis using an antiserum specific to IIM. For Western blot analysis, the larvae were homogenized in 100 ul of SDS/PAGE sample buffer. Subsequently, 4 $\mu$l of each sample was electrophoresed through a 7.5% SDS/PAGE gel, blotted, and then probed with anti-IIM antiserum.

To assess the correlation between the extent of IIM degradation in living insects and the degree of enhanced AcMNPV infection by TnGV enhancin, 60 neonate larvae from each feeding group were also collected and individually reared on artificial diet. Viral infections were monitored and examined throughout the whole insect larval developmental stages, as described by Wang et al. The extent of degradation of IIM was correlated with increased AcMNPV infection in larvae. This enhanced mortality was statistically significant and can be presented by the regression analysis: Probit mortality=4.72+0.256×enhancin dose (ng/larva) ($R2$=99.2; P=0.004).

The in vivo IIM degradation assay was also conducted by feeding fifth instar *Trichoplusia ni* larvae with TnGV enhancin and analyzing the residual IIM in the fecal pellets. Early fifth instar *Trichoplusia ni* larvae were fed 10 ul of inoculum containing 5% sucrose, 10 $\mu$g/ml blue food coloring, and 5 $\mu$g TnGV enhancin in 25 mM sodium carbonate buffer (pH 10.5). Afterward, the larvae were transferred to individual rearing cups containing artificial diet and incubated at 28° C. During the incubation period, enhancin will digest the IIM present in the PM. PMs are secreted within the intestine and later excreted with fecal pellets, which are normally ensheathed within the remnants of a PM. The first three fecal pellets marked with blue food coloring therefore were collected and subjected to Western blot analysis using the IIM-specific antiserum. The in vivo IIM-degradation assay using fifth instar larvae showed that IIM was present in the control fecal pellets and exhibited some minor degradation. However, no IIM was detected in the fecal pellets collected from the TnGV enhancin-fed larvae, confirming that enhancin completely degraded IIM in the digestive tract of living insects.

It has been reported that in insects' PMs shield the midgut epithelial surfaces and can provide some level of protection from microbial invasion and infection. The present study extends previous work on the degradation of PM proteins by a baculovirus enhancin by demonstrating that an intestinal mucin (IIM), the major PM protein in *Trichoplusia ni* larvae, is the target substrate for the enhancin. The degradation of mucin leads to the disruption of this intestinal barrier and supports the proposed mode of action for enhancing. The presence of an IIM protein and its degradation by enhancin is not restricted to the species, *T. ni*. Another mucin, similar to the IIM from *Trichoplusia ni* PMs, was also isolated from *Pseudaletia unipuncta* PMs and biochemically characterized. This mucin is also degraded by the TnGV enhancin and degradation was correlated with enhanced baculovirus infections in *P. unipuncta* larvae.

*Trichoplusia ni* PMs are present in all larval instars and at all stages between molts. Therefore, IIM may play a protective role throughout the entire larval period. No mucin degrading protease has been previously reported to be associated with a virus to assist the penetration of a pathogen through a mucinous protective barrier; therefore, this study represents a novel concept in animal virus pathogenesis. The present invention enables further studies on the specific recognition sites and cleavage of mucins by baculovirus enhancing, and the biological properties of IIM and enhancing. Furthermore, use of IIM degrading enzymes in recombinant plants or baculoviruses will decrease larval growth and increase the pathogenesis of virus infections.

Diet Incorporation Experiments Using Anti-IIM Serum

Polyclonal antibodies against an insect peritrophic membrane (PM) protein from the Australian blowfly, *Lucilia cuprina* inhibited growth and caused mortality of blowfly larvae. It was reported that this biological response was caused by the PM antibody, which blocked nutrient diffusion across the PM. The present invention includes the discovery that a polyclonal antibody against the *Trichoplusia ni* PM mucin (IIM) has an adverse effect on *Trichoplusia ni* growth and survival.

Mucin was prepared from *Trichoplusia ni* fifth instar larval PM by preparative PAGE. The gel was stained by $CuCl_2$ (0.3M) for 5 min and the band containing mucin was isolated and destained in 0.2 M EDTA. Mucin was further eluted from the gel slices by electroelution, and used to immunized rabbit following a standard rabbit immunization protocol. 0.2 mg mucin was used per injection for a total of 3 injections. Serum was collected at 6 weeks after the first injection and IgG was purified from the serum using caprylic acid and ammonium sulfate methods (Harlow, E. & Lane, D. 1988—Antibody, a laboratory manual. Cold Spring Harbor Laboratory). Control rabbit IgG was also purified from normal rabbit serum (Gibco).

A laboratory colony of *Trichoplusia ni* reared on high wheat germ diet was used in these experiments. To prepare diet incorporated with IgG, high wheat germ diet was prepared but with less water (10% less than the final diet volume). After mixing all the components, the diet was allowed to cool gradually to 45° C., and IgG solution was added with vigorous stirring. Heat inactivation experiments showed that the immunoreactivity of the anti-IIM serum was reduced above 60° C. (data not shown). Water was added when necessary to adjust the volume. The diet prepared in this way has exactly the same concentration of each component as normal high wheat germ diet, with the exception of the addition of IgG. The final concentration of IgG in the diet was 20% of the original IgG concentration (V/V) in original anti-IIM serum. The diet was aliquoted (2.5 mls/cup) into 1 oz cups which was sufficient diet to allow the larvae to develop into pupae.

*Trichoplusia ni* neonates were placed individually into the cups with standard (no IgG) or IgG-incorporated diet. This time point was designated as time zero. The larvae were incubated at 28° C. and the larval growth was recorded every 8 hours. The larval weight was also recorded at the3rd and 6th day. Pupal weight was measured when all the larvae had pupated. The experiment was conducted twice with 30 insects per treatment.

Incorporation of IgG into the diet had a significant effect on *Trichoplusia ni* larval development (Table 1). Although control rabbit IgG containing diet had a strong effect on larval growth compared to larvae on standard wheat germ diet, the anti-IIM IgG treatment had an even stronger and statistically significant effect. The duration of growth from neonate to pupa was delayed in anti-IIM IgG fed larvae, and was significantly longer than control IgG containing diet fed larvae. Similarly, the anti-IIM IgG fed larvae had the lowest weight at day 3 and day 6, and their weight was also significantly lower than larvae fed on control IgG diet at day 6 in both experiment and at day 3 for experiment 2. No difference in pupal weight was found between all the treatments in both experiments.

TABLE 1

Comparison of *Trichopusia ni* larval and pupal weights and develpmental duration from neonate to pupa

| Treatment | # of insect | Duration from Neonates to Pupae (hr ± SE) | p* | Larval Weight at Day 3 (mg ± SE) | p* | Larval Weight at Day 6 (mg ± SE) | p* | Pupal Weight (mg ± SE) | p* |
|---|---|---|---|---|---|---|---|---|---|
| Exp. 1-Control | 30 | 201.47 ± 1.71 | 0.05 | 6.45 ± 0.49 | 0.11 | 142.50 ± 7.35 | 0.01 | 225.57 ± 3.43 | 0.62 |
| Exp. 1-Normal IgG | 30 | 212.48 ± 2.78 | | 3.91 ± 0.33 | | 93.65 ± 6.93 | | 221.16 ± 2.94 | |
| Exp. 1-Anti-IIM IgG | 30 | 219.07 ± 1.79 | | 3.28 ± 0.19 | | 72.47 ± 4.23 | | 223.28 ± 3.10 | |
| Exp. 2-Control | 30 | 193.6 ± 1.46 | 0.02 | 5.78 ± 0.30 | 0.02 | 167.17 ± 6.26 | 0.03 | 223.83 ± 3.21 | 0.45 |
| Exp. 2-Normal IgG | 30 | 206.90 ± 2.91 | | 3.99 ± 0.24 | | 112.93 ± 9.39 | | 224.20 ± 3.04 | |
| Exp. 2-Anti-IIM IgG | 30 | 216.53 ± 2.82 | | 3.17 ± 0.24 | | 88.95 ∓ 6.82 | | 227.70 ± 3.29 | |

*From t-test comparing weight or duration between larvae on normal IgG diet and anti-IIM IgG diet.

An effect of anti-IIM IgG on *Trichoplusia ni* larval development was observed in both diet incorporation experiments. Compared with larvae fed on control rabbit IgG containing diet, the larvae on anti-IIM IgG containing diet required a longer time to develop from a neonate to pupa, and had a lower larval weight at day 3 and day 6. In most cases, the differences were statistically significant. Since no difference in pupal weight for the various treatments was observed, the differences in larval weight might be caused by a difference in speed of development. It is clear that the presence of anti-IIM IgG in the diet resulted in significantly slower growth of *Trichoplusia ni* larvae. Anti-IIM IgG binds to the major protein on the insect peritrophic matrix, which could result in the blockage of nutrient flow through the peritrophic matrix.

In the current study it was observed that control rabbit IgG had a significant effect on larval development, compared with larvae growing on standard high wheat germ diet. Several different commercial rabbit sera were compared (two batches from Sigma, and one from Gibco), and they all showed a similar effect on *Trichoplusia ni* development (data not shown). The reason for this is not clear. No major cross-reaction of normal rabbit IgG to *Trichoplusia ni* peritrophic matrix components was detected in western blot experiments (data not shown). It is possible that IgG somehow interferes with the digestive physiology of the insect, or has some feeding deterrent effect. A similar phenomena was also reported by Casu, et al. (1997) where the growth of the blood feeding insect, Lucilia cuprina was inhibited in the presence of high concentration of normal control IgG.

The design of the experiments conducted were effected by the relatively low amount of serum that can be obtained from rabbits (ie., 70 mls/rabbit) for use in experiments. In a prior report the inventors demonstrated (using a PM permeability chamber) that anti-IIM serum could block the permeability of the PM to particles smaller than 5 nm. This demonstrates that such a phenomenon, if it occurred in vivo, might have a detrimental effect on the nutritional physiology of the insect. These data (together with the published Australian work) demonstrates that the delivery of anti-IIM antibodies through transgenic plants might be a novel approach for affecting insect development or mortality.

Altered In situ Peritrophic Membrane Permeability

The present invention includes the discovery that feeding larvae anti-IIM-IgG affects the permeability of the peritrophic membrane.

Fifth instar larvae reared on a high wheat germ diet were starved for 1 hours. Starved larvae were then injected per os with 20 μl of anti-IIM IgG (2×concentrated) solution and placed on a high wheat germ diet containing an equivalent of 20% anti-IIM IgG and 4% (dry wt) FITC-Dextran (3.2 nm diam.). Controls larvae were injected per os with either PBS or normal serum IgG and placed on their respective diets. After feeding for 2.5 hours at 28° C., larvae were chilled on ice and dissected under saline buffer to expose the alimentary canal. Once the esophagus and proctodeaum were ligated, a small hole (0.2×2 mm) was made to expose the PM. This hole was made in the middle portion of the midgut just immediately anterior to the anastomosing malpighian tubules. These mesenterons were then severed from the alimentary tract and placed in a small dish which contained 15-ml buffer. To help remove any free FITC-dextran, the ligated midgut was rinsed 3 times with 15-ml aliquots of buffer. When the final rinse solution was removed, the ligated midgut was re-suspended in 4 ml of saline buffer and incubated under gentle mixing. Aliquots of incubating solutions were removed every 0.5 hours and measured for the amount of fluorescence using a fluorescent plate reader set at a 485-nm excitation of 530-nm emission.

Figure 2:
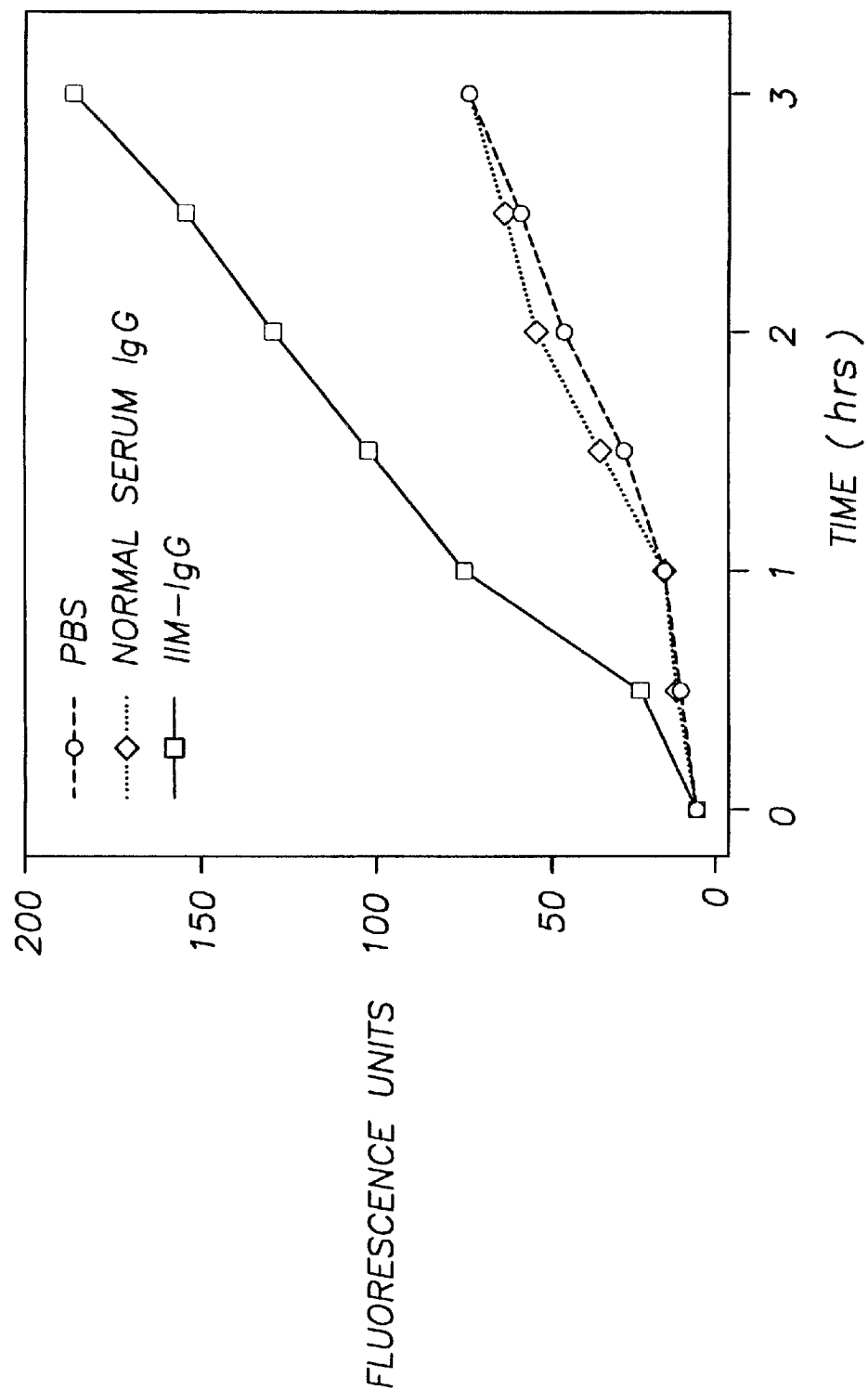

The permeability characteristics of PMs to passage of FITC-dextran is presented below. *Trichoplusia ni* larvae fed on diets containing IIM-IgG showed greater amounts of FITC-dextran in the incubating buffer as compared to those larvae fed on diets containing normal serum and PBS (FIG. 1). Intact, lighted midgut showed FITC-dextran is confined within the midgut proper and that the midgut wall acts as a barrier to the 3.2 nm FITC-dextran. FIG. 2 shows permeability characteristics of ligated midgut from larvae fed diet containing either IIM-IgG, normal serum IgG, or PBS. An intact, ligated midgut (PBS–No Portal=PM not exposed) showed low passage of FITC-dextran across midgut wall.

Figure 3:
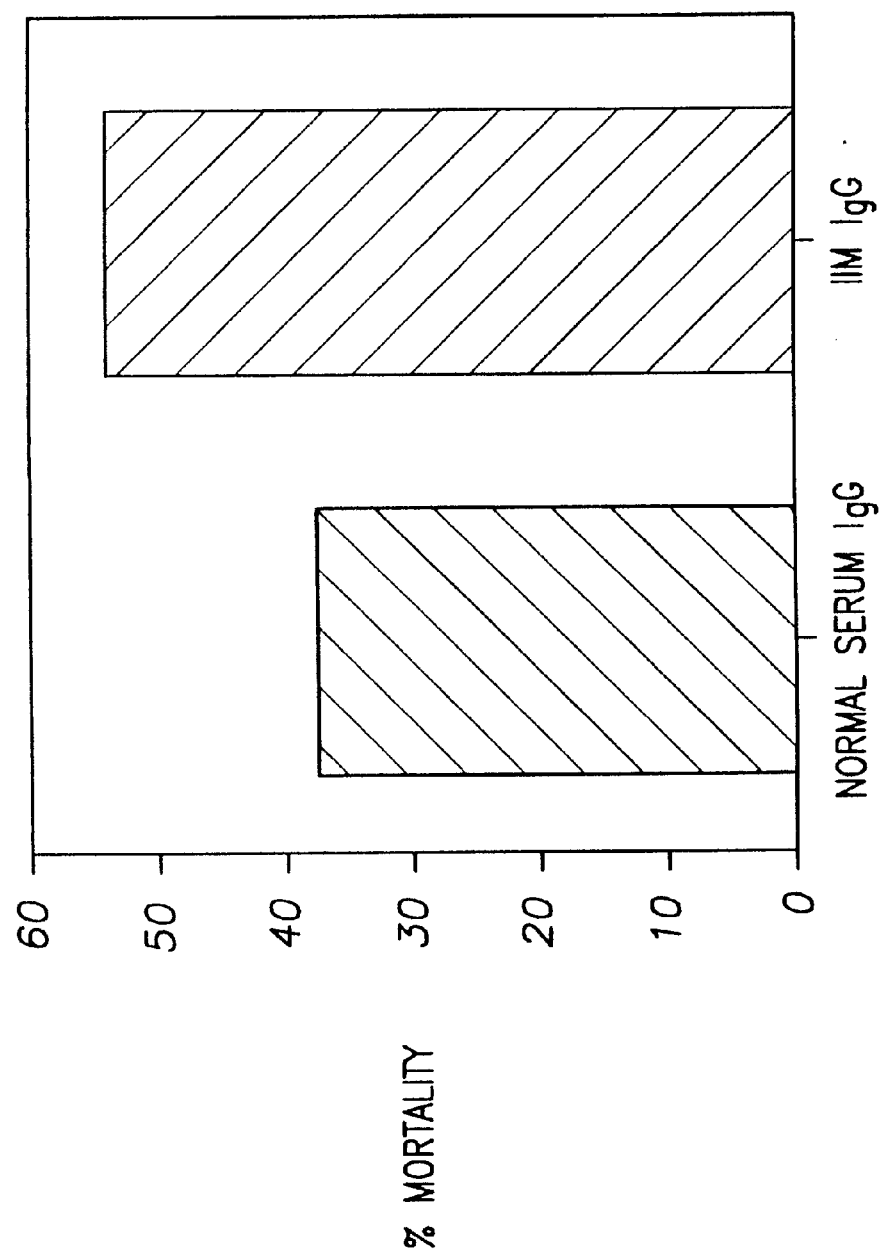

Similar results were obtained in a another ligation experiment. Again, there was more FITC-dextran present in the incubation buffer of IIM-IgG ligated midgut. FIG. 3 shows permeability characteristics of ligated midgut. Larvae were fed diets containing either IgG isolated from normal or anti-IIM serum or PBS. Each treatment and control are replicated.

Preliminary results show insect larvae that have fed on diets containing IIM-IgG have a greater PM permeability to FITC-dextran. In both experiments the final amount of fluorescence in the incubating medium (at 3 h) was greatest from IIM-IgG fed insects. One possible explanation for this is that ingested IgG may bind to newly secreted IIM thus altering the amounts of protein matrix available for normal PM synthesis. These results are contradictory when compared to previous studies, which demonstrated the blocking ability of anti-IIM to passage of FITC-dextran. In those in vitro studies, PMs were dissected and treated with serum. In the present ligation studies, insects are fed IIM-IgG for 2.5 hours. Therefore, IgG may bind to delaminated PM resulting in a "short term blockage" which could be followed by a subsequent "long term structural alteration" of PM. PM alterations could result from antibody competing for IIM (especially during PM formation). These interactions could produce very porous PMs. IIM-IgG induced PM structural abnormalities may be an appropriate explanation for the observed weight changes and increased development time of larvae from the diet incorporation experiments. Future research from this laboratory should included a TEM study which would examine PM morphology of insects which have fed on diets containing IgG. If anti-IIM is competing with mucin then altered PM morphology is expected.

The role of IIM in the permeability of *T. ni* PMs when treated with enhancin was investigated further. Untreated *T. ni* PMs were exposed to R18-labelled AcMNPV PDV for 8 hours at the lumen side. PDV was not detected in samples from the epithelial side of PM, although low levels of R18-labelled virus were detected after 24 hours. When PMs were treated with enhancin, R18-labelled virus particles readily crossed the PMs as indicated by an increase in fluorescence after 2 hours. *T. ni* neonate bioassays confirmed that enhancin may promote increased poration within the PM matrix, thus influencing the permeability of PMs to PDV. The PDV that crossed enhancin treated *T. ni* PMs was infectious, as was demonstrated by increased mortality rates compared to control treatments (Table 2). The effect of enhancin on PM permeability to infectious viruses was confirmed using a second insect species, *P. unipuncta*. Enhancin had a significant effect on PM permeability, although the *P. unipuncta* PMs appeared to be more permeable to the virus (Table 2).

In lepidopterous larvae, the PM is a structure containing pores which may vary in size among different insect species. Low level permeability of untreated *T. ni* PMs to blue dextran 2000 appears to confirm the presence of naturally occurring pores within the PM matrix. Although the purpose of this study was not to determine the approximate pore size of *T. ni* or *P. unipuncta* PMs, these studies did show that control *T. ni* PMs were permeable to blue dextran (diameter: 54nm) but were almost impermeable to AcMNPV PDV (186 nm diameter×357 nm length, unpublished data) over an 8-hour period. Insect bioassays also suggested that untreated *P. unipuncta* PMs probably had a larger pore size and allowed passage of more PDV particles than PMs from *T. ni* since control mortality values were higher for samples obtained from *P. unipuncta* PM permeability experiments (1% vs. 38%, respectively; Table 2).

TABLE 2

*Trichoplusia ni* neonate bioassays showing increased permeability of *Trichoplusia ni* and *Pseudaletia unipuncta* peritrophic matrix to AcMNPV PDV following tratment with enhancin.

| | T. ni Peritrophic Matrix[a] | | | P. unipuncta Peritrophic Matrix[b] | | |
|---|---|---|---|---|---|---|
| Treatment | Total Insects Tested | Avg. % Morality ± SE | t-Test (p) | Total Insects Tested | Avg. % Morality ± SE | t-Test (p) |
| PM[c] enhancin treated | 90 | 15.6 ± 2.9 | <0.01 | 150 | 90.7 ± 2.9 | <0.01 |
| PM control | 90 | 1.0 ± 0.3 | | 150 | 38.0 ± 8.2 | |

TABLE 2-continued

Trichoplusia ni neonate bioassays
showing increased permeability of
Trichoplusia ni and Pseudaletia unipuncta
peritrophic matrix to AcMNPV PDV
following tratment with enhancin.

| | T. ni Peritrophic Matrix[a] | | | P. unipuncta Peritrophic Matrix[b] | | |
|---|---|---|---|---|---|---|
| Treatment | Total Insects Tested | Avg. % Morality ± SE | t-Test (p) | Total Insects Tested | Avg. % Morality ± SE | t-Test (p) |
| AcMNPV PDV control | 90 | 97.8 ± 2.2 | | 150 | 100 ± 0 | |

[a]Summary of 3 independent tests.
[b]Summary of 5 independent tests.
[c]PMs mounted in a dual chamber permeability apparatus were treated with 3 mg/ml enhancin for 1 hour and samples were collected 16 hours post-treatment.

Earlier studies from our laboratory demonstrated that sephacryl-purified enhancin preparations contained traces of contaminating insect proteases. In a subsequent study, Lepore et al. (1996) showed that extensive purification of enhancin by ion exchange chromatography and immobilized α-macroglobulin removed the contaminating proteases without diminishing the in vivo and in vitro activity of enhancin, thus providing evidence that these proteases did not have a role in the enhancement of infections. Furthermore, in that same study, Lepore, et al. (1996) also demonstrated that purified TnGV enhancin, expressed by a recombinant AcMNPV in insect cells, was active on insect PMs.

Addition of protease inhibitors provided evidence that potential contaminating proteases did not have a role in increasing the PM permeability. The metalloprotease inhibitor EDTA was able to inhibit the action of enhancin. Although there is no published evidence that granulosis viruses encode a chitinase, it was recently reported that such a functional gene was present in the nuclear polyhedrosis virus, AcMNPV. To rule out the effect of any possible chitinase contamination in our enhancin preparation a potent chitinase inhibitor was used and no effect on the ability of enhancin to increase PM permeability was found. Chitinase activity was not detected in our preparations using a chitinase activity assay.

Previous studies with enhancin suggested that the PM, though clearly not an impenetrable barrier, does reduce the exposure of susceptible midgut cells to baculoviruses. It appears that some insect viruses may have evolved similar mechanisms to degrade the structural integrity of the PM and facilitate the passage of infectious virus. Derksen and Granados (1988) reported that an unidentified factor in the polyhedrin fraction of AcMNPV was able to affect the protein profile and structure of the PM. This observation was recently confirmed by Faulkner et al. (1997) who found that OBs from both a mutant and wild-type AcMNPV could degrade the PM from T. ni larvae. Furthermore, the presence of an enhancin-type gene was recently reported from Lymantria dispar nuclear polyhedrosis virus suggesting that other similar nuclear polyhedrosis viruses (NPVs) may carry enhancin genes. Begon et al. (1993) reported Plodia interpunctella GV (PiGV) OBs caused dramatic and significant effects of the PM structure from the same species and concluded that the PM provided a barrier to PiGV infection at lower virus doses.

There have been many investigations concerning the mode of action of enhancin, but a consensus has not been reached. It was previously reported that an enhancin from PuGV acted on the plasma membrane of midgut cells and cultured insect cells, facilitating the entry of virus particles into the cells by providing attachment sites or facilitating membrane fusion for the virus particles. Based upon a series of studies, including this report, we believe a major role of GV enhancins is to disrupt the structural integrity and increase the permeability of the PM to baculovirus particles. Our previous studies demonstrated that enhancin from TnGV digested a specific major PM protein, insect intestinal mucin. The digestion of this PM mucin and the resulting degradation of the PM structure was correlated with enhanced baculovirus infection of insect larvae. It is reasonable to conclude that the disruption of the PM structure resulted in the increased porosity of the PM, thereby facilitating the infection of the underlying epithelial cells. Thus, these viral-encoded proteins appear to play an important role in baculovirus pathogenesis.

Ubiquity Of Mucins In Insect Species

T. ni mucin or IIM is an integral peritrophic membrane or matrix (PM) protein. IIM with its cysteine rich domains, apparently binds chitin to form a strong semipermeable structure which partitions ingested food and microbes from the midgut epithelium and may aid in digestion. The inventors examined the distribution of mucin (IIM) in different insect species.

TABLE 3

| Commonname | Genus species | Family | Cross Reactivity with anti-IIM |
|---|---|---|---|
| Cabbage looper | Trichoplusia ni | Noctuidae | yes |
| Armyworm | Pseudaletia unipuncta | Noctuidae | yes |
| Tobacco budworm | Heliothis virescens | Noctuidae | yes |
| Black cutworm | Agrotis ipsilon | Noctuidae | yes |
| Beet armyworm | Spodoptera exigua | Noctuidae | yes |
| Fall webworm | Hyphantria cunea | Arctiidae | yes |
| Banded woollybear | Pyrrharctia isabella | Arctiidae | yes |
| Imported cabbageworm | Pieris rapae | Pieridae | ? |
| Common white butterfly | Pieris napi | Pieridae | |
| Silkworm | Bombyx mori | Bombycidae | yes |
| European corn borer | Ostrinia nubilahs | Pyralidae | yes |
| Monarch butterfly | Danus plexippus | Danaidae | yes |
| Gypsy moth | Lymantria dispar | Lymantriidae | yes |

TABLE 3-continued

| Commonname | Genus species | Family | Cross Reactivity with anti-IIM |
|---|---|---|---|
| Potato tuberworm | Phthorimaea operculella | Gelechiidae | yes |
| Diamondback moth | Plutella xylostella | Plutellidae | yes |
| House fly | Musca domestica | Muscidae | yes |
| Tarnished plant bug | Lygus lineolaris | Miridae | yes |
| Sweet potato whitefly | Bemisia tabaci | Aleyrodidae | yes |
| English grain aphid | Sitobion avenae | Aphididae | yes |
| American cockroach | Periplaneta americana | Blattidae | yes |
| German cockroach | Blattella germanica | Blattellidae | yes |
| Fruitfly | Drosophila melanogaster | Drosophilidae | ? |
| Yellowfever Mosquito | Aedesaeqypti | Culicidae | ? |
| Fungus gnat | Bradysia ssp. | Sciaridae | no |
| Colorado potato beetle | Leptinotarsa decemlineata | Chrysomelidae | no |
| Western spotted cucumber beetle | Diabrotica undecimpunctata undecimpunctata | Chrysomelidae | no |
| Mealybug | Planococcus citri | Pseuclococcidae | no |

Insect midgut was dissected to remove the PM. PM proteins were solubilized in SDS sample buffer containing mercaptoethanol. Supernatants were subjected to SDS-PAGE, blotted onto nitrocellulose membranes, probed with a Polyclonal anti-IIM antibody preparation, washed, and incubated in a secondary antibody labeled with alkaline phosphatase. Bands were visualized by the addition of NBT/BCIP solution to the blots.

76% of the insect species tested (16/21) possess protein or protein moeites which cross reacted with anti-IIM antibody. Table 1 lists the insect species tested for the presence of mucin. PMs were examined in all insects except for mealy bugs and sweet potato whitefly where the whole insect was used. Only midguts of Lygus bugs were extracted and examined for the presence of IIM.

Examination of blots showed the presence of strong to weak signals. Immunoreactive band development was strong in the tobacco budworm, fall armyworm, banded woollybear, armyworm and cabbage looper. The remainder (listed below) gave moderate, weak or no cross reactivity to anti-mucin antibody. Also, some insects had high molecular weight bands similar in size to T. ni IIM (denoted by asterix)

| Strong Band Development | Weak Reactivity |
|---|---|
| * Tobacco budworm | * European corn borer |
| * Fall armyworm | * Monarch butterfly |
| * Banded Woollybear | American cockroach |
| * Armyworm | Beet armyworm |
| * Cabbage Looper | |

| Moderate Reactivity | No Reactivity |
|---|---|
| * Black cutworm | Imported cabbageworm |
| * Gypsy moth | Mealybug |
| House fly | Fungus gnat |
| German cockroach | Colorado potato beetle |
| Tarnished plant bug | |
| Diamondback moth | |
| Potato tuberworm | |
| Whitefly | |

* = possess bands which are around 400 kD

These studies have demonstrated that mucin (IIM) or mucin-like PM proteins are present in a wide variety of insect species in 5 orders. These insects and possibly many other species may share common mechanisms which involve mucin or mucin like proteins which bind chitin thus permitting the formation of PM. It is interesting to note that a Homopteran and a Hemipteran possess discrete bands which cross react with anti-IIM antibody. This is interesting observation since these insects may not produce a PM as found in other insects. Some investigators feel these insects may produce an extracellular secretions which may be functional analogues to the chitinous PM. Based on our observations, there may exits in Homopterans and Hemipterans a protective barrier present which contains mucin-like proteins.

Two potential relevant applications exist to this work. First, those insects which cross react with anti-IIM may be sensitive to the PM degrading molecule, enhancin and secondly. these same insect PMs may be susceptible to antibody binding which would reduce nutrient assimilation thus leading to a pre-reproductive growth or death.

Transgenic Plants Expressing IIM-IgG

The present invention includes a transgenic plant that express IIM-IgG. Since the immunotherapeutic potential of antibodies produced In plants has been demonstrated in a number of cases, we believe that using peritrophic matrix IIM-specific Ab in plants could be used as immunocontrol strategy for control of insect pests. The concept of using PM Ab to control insect pest has been established in the case of insects which are pest of animals. Researchers in Australia have shown that PM proteins injected into sheep produce antibodies that interfere with the growth or even kill the fly pest, Lucilia cuprina that causes cutaneous myiasis in the sheep, a conditions that causes over 200 million dollars in losses per year. These researcher provided evidence that the Ab were able to interfere with the porosity of the fly PM and interfered with the normal digestive processes of the insect. They speculated that this type of approach could be used in plants to control insects.

A transgenic plant expressing IIM-IgG can be constructed using available techniques for inserstion of cDNA encoding an antibody to IIM into a plant genome.

Accordingly, it is to be understood that the embodiments of the invention herein described are merely illustrative of the application of the principles of the invention. Reference herein to details of the illustrated embodiments are not intended to limit the scope of the claims, which themselves recite those features regarded as essential to the invention.

What is claimed is:

1. An isolated polynucleotide encoding an invertebrate intestinal mucin comprising an amino acid sequence selected from the group consisting of:
   a) SEQ ID No. 3; and
   b) SEQ ID No. 4.

2. An isolated polynucleotide encoding an invertebrate intestinal mucin, said polynucleotide comprising a nucleotide sequence selected from the group consisting of:
   a) SEQ ID No. 1; and
   b) SEQ ID No. 2.

3. An expression vector comprising an expression control sequence operatively linked to the polynucleotide of claim 1 or claim 2.

4. An isolated host cell comprising the expression vector of claim 3.

5. The expression vector of claim 3, wherein the expression vector is a bacterial expression vector.

6. The expression vector of claim 3, wherein the expression vector is a plant expression vector.

7. A method of producing an invertebrate intestinal mucin protein or peptide comprising:

a) transforming a host cell with an expression vector comprising a promoter operatively linked to a nucleotide sequence, wherein the nucleotide sequence encodes an amino acid sequence selected from the group consisting of:
   i) SEQ ID No. 3; and
   ii) SEQ ID No. 4;
or wherein the nucleotide sequence encodes a peptide comprised by a sequence selected from the group consisting of:
   iii) SEQ ID No. 3; and
   iv) SEQ ID No. 4;

b) culturing said host cell under conditions that allow expression of said invertebrate intestinal mucin protein or peptide in recoverable quantity;

c) lysing said host cell; and d) recovering said invertebrate intestinal mucin protein or peptide.

8. The method of claim 7 wherein said expression vector encodes a fusion protein comprising the invertebrate intestinal mucin protein or peptide and glutathione-S-transferase.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 2455 base pairs
       (B) TYPE: nucleic acid
       (C) STRANDEDNESS: double
       (D) TOPOLOGY: linear (ii) MOLECULE TYPE: cDNA (iii) HYPOTHETICAL: NO (iv) ANTI-SENSE: NO (v) FRAGMENT TYPE: N-terminal (vi) ORIGINAL SOURCE:
       (A) ORGANISM: Trichoplusia ni
       (F) TISSUE TYPE: Peritrophic Membrane (vii) IMMEDIATE SOURCE:
       (B) CLONE: IIM14

(xi) SEQUENCE DESCRIPTION: SEQ ID NO:1:

```
GTAACGTTAA GTGAAAAGAA TAACCAGCGA ACAAGTTATG ATAAAGACCC TCCTATTCCT      60
GACGGCCCTC GGGCTCGTCG CCGCGCGTCC TGAAGTCAGC GACGCGGAGA AGAACCCCGC     120
TCTCCACGAG CCGCACCCAG ACTGCCCTCC CGCTGAGCAG CACTGGCTCC TGCCTCACGA     180
ATACGACTGC ACCAAGTTCT ACTACTGTGA ATATGGTCTC AAGTTCATCG CACCGAGAGA     240
CTGTGCTCCT GGTACCGAAT TCAAGTTCTC CGCTCAGACT TGTGTTCACG CCGCTTTAGC     300
CGGATGCACC CTGCCAGGAC CTCCAGCTGA GACAACCCAG GCCCCAGCAA CAACTCAGGC     360
CCCAACAACC ACCCAGGCCC CAACCACAAC TACTCAGGCC CCTACTACAA CCACCCAGGC     420
CCCAACCACA ACCACCCAGG CCCCAACCAC CACCCAGGCC CCAACCACCA CCCAGGCCCC     480
AACTACCACT CAGGCCCCTA CTACTACCAC TCAGGCCCCA ACCACAACCA CTCAGGCCCC     540
TACCACAACC ACCCAGGCCC CAACCACCAC CCAGGCCCCA ACTACCACCC AGGCCCCAAC     600
TACCACTCAG GCCCCAACTA CAATCACCCA GGCTGCAACT ACCCCGGCCG CAACTACCCC     660
GGCCGCAACT ACCCCGGCCG CAACTACCCC TGCCGCGACA ACCCCGCTG CAACTACCCC      720
AGGTGTTCCT GCACCCACTT CAGCCCCAGT CTGGCCCCCG ATCTGTGAAC TGTTGCCCAA     780
TGGTTGCCCA GCTGACTTCG ACATCCACTT GTTGATTCCC CACGACAAGT ACTGCAACCT     840
CTTCTACCAG TGCTCCAACG GTTACACCTT CGAACAGAGG TGCCCTGAGG GACTCTACTT     900
CAACCCCTAC GTCCAGCGCT GCGACTCTCC TGCTAACGTT GAATGCGACG GCGAAATCAG     960
CCCCGCACCC CCAGTCACAG AAGGCAACGA AGACGAAGAC ATTGACATCG GAGACCTCCT    1020
CGACAATGGA TGCCCAGCTA ACTTCGAAAT CGACTGGCTC TTGCCCCACG GAAACCGTTG    1080
CGACAAGTAT TACCAGTGCG TCCACGGTAA CTTGGTAGAG AGGCGTTGTG GAGCCGGCAC    1140
CCACTTCAGT TTTGAACTTC AGCAATGTGA CCACATCGAG CTCGTTGGCT GCACCCTCCC    1200
CGGCGGCGAG AGCGAAGAAG TTGACGTCGA CGAGGATGCC TGCACCGGCT GGTACTGCCC    1260
CACGGAACCC ATTGAATGGG AGCCCCTCCC CAACGGCTGC CCTGCCGACT TCAGCATCGA    1320
CCACCTCCTC CCCCACGAGA GCGACTGCGG CCAGTATCTA CAGTGTGTCC ATGGACAGAC    1380
```

```
TATCGCAAGA CCTTGCCCTG GAAACCTGCA CTTCAGTCCT GCCACACAGT CCTGTGAGTC    1440

TCCTGTGACC GCTGGTTGCC AAGTTTTCGA GTGCGATTCT GACAACCAGT GCACATCGAC    1500

TGCTGCCCCG ACAGCTGCTC CAACGGCTGC CCCAACGGCT GCCCCAACGG CTGCCCCAAC    1560

TGCCGCACCC TCCACCGTGG TCCCACCTGC AACGCCACCC GCAACTGCAG CCCCAGTCCC    1620

ACCTACAACC GCAATTCCTA CTCCGGCCCC CACCGCTGCC CCACCGCAG CTCCTACTAC    1680

TGCTGCCCCT GAATCCCCAA CCACTGTCAC AGTACCACCT ACTGCTGCTC CCACCGCAGC    1740

CCCTACTACT GCTGTCCCTG AAATCCCAAT CACTGTCACA TCAGCGCCTA CCGCTGCCCC    1800

CACCGCTGCC CCCACCGCTG CCCCCACCGC AGCCCCTACT ACTGCTGTCC CAGAAATCCC    1860

AACTACTGTC ACATCACCAC CTACTGCTGC CCCCACTACC GCAGCACCTG CCCCAACAC    1920

CACAGTCACT GTACCACCCA CTGCTGCCCC TACTACCGCA GCACCTGCCC CCAACACCAC   1980

AGTCACTGTA CCACCCACTG CTGCCCCCAC TGCAGCTCCC CCTACCGTCG CACATGCACC   2040

CAACACCACA GCTGCCCCGG TAACTACAAC CAGCGCACCA GCTACCACAC CTGAAGATGA   2100

TGACATCGAC CCCCCTCTCC CCAACGACCC CATCAACCCT TGCGTTGAAG AATGCAACGT   2160

TTTGCCCTGG GCTCACGCTG ACTGCGACAA ATACTGGGTC TGTGACGGCA ACAACCAAGT   2220

CCTGGTGGTT TGCTCTGAGG GTCTCCAGTT CAACCCCACT ACTAAGACCT GTGACTTCGC   2280

TTGCAACGTC GGTTGCGTGA GGAGCAACAT TCAGATGTCT GAAAGCTACG AAGGAGTCCA   2340

GGTCTTCATC CCATGGAACA AACTAGATGA AGACATCAGA CAGGCGCTGA ACTTTGAGTT   2400

GTAAACCTAC TTAAATTAAT GAAGGTTTTG TTTTAAAAAA AAAAAAAAAA AAAAA       2455

(2) INFORMATION FOR SEQ ID NO:2:

(i) SEQUENCE CHARACTERISTICS:
        (A) LENGTH: 2821 base pairs
        (B) TYPE: nucleic acid
        (C) STRANDEDNESS: double
        (D) TOPOLOGY: Not Relevant (ii) MOLECULE TYPE: cDNA (iii) HYPOTHETICAL: NO (iv) ANTI-SENSE: NO (v) FRAGMENT TYPE: N-terminal (vi) ORIGINAL SOURCE:
        (A) ORGANISM: Trichoplusia ni
        (D) DEVELOPMENTAL STAGE: larva
        (F) TISSUE TYPE: peritrophic membrane (xi) SEQUENCE DESCRIPTION: SEQ ID NO:2:

GAAAAGAATA ACCAGCGAAC AAGTTATGAT AAAGACCCTC CTATTCCTGA CGGCCCTCGG      60

GCTCGTCGCC GCGCGTCCTG AAGTCAGCGA CGCGGAGAAG AACCCCGCTC TCCACGAGCC     120

GCACCCAGAC TGCCCTCCCG CTGAGCAGCA CTGGCTCCTG CCTCACGAAT ACGACTGCAC     180

CAAGTTCTAC TACTGTGAAT ATGGTCTCAA GTTCATCGCA CCGAGAGACT GTGCTCCTGG     240

TACCGAATTC AAGTTCTCCG CTCAGACTTG TGTTCACGCC GCTTTAGCCG GATGCACCCT     300

GCCAGGACCT CCAGCTGAGA CAACCCAGGC CCCAGCAACA ACTCAGGCCC AACAACCAC      360

CCAGGCCCCA ACCACAACTA CTCAGGCCCC TACTACAACC ACCCAGGCCC CAACCACAAC     420

CACCCAGGCC CCAACCACCA CCCAGGCCCC AACCACCACC CAGGCCCCAA CTACCACTCA     480

GGCCCCTACT ACTACCACTC AGGCCCCAAC CACAACCACT CAGGCCCCTA CCACAACCAC     540

CCAGGCCCCA ACCACCACCC AGGCCCCAAC TACCACCCAG GCCCCAACTA CCACTCAGGC     600
```

-continued

```
CCCAACTACA ATCACCCAGG CTGCAACTAC CCCGGCCGCA ACTACCCCGG CCGCAACTAC      660

CCCGGCCGCA ACTACCCCTG CCGCGACAAC CCCCGCTGCA ACTACCCCAG GTGTTCCTGC      720

ACCCACTTCA GCCCCAGTCT GGCCCCCGAT CTGTGAACTG TTGCCCAATG GTTGCCCAGC      780

TGACTTCGAC ATCCACTTGT TGATTCCCCA CGACAAGTAC TGCAACCTCT TCTACCAGTG      840

CTCCAACGGT TACACCTTCG AACAGAGGTG CCCTGAGGGA CTCTACTTCA CCCCTACGT       900

CCAGCGCTGC GACTCTCCTG CTAACGTTGA ATGCGACGGC GAAATCAGCC CCGCACCCCC      960

AGTCACAGAA GGCAACGAAG ACGAAGACAT TGACATCGGA GACCTCCTCG ACAATGGATG     1020

CCCAGCTAAC TTCGAAATCG ACTGGCTCTT GCCCCACGGA AACCGTTGCG ACAAGTATTA     1080

CCAGTGCGTC CACGGTAACT TGGTAGAGAG GCGTTGTGGA GCCGGCACCC ACTTCAGTTT     1140

TGAACTTCAG CAATGTGACC ACATCGAGCT CGTTGGCTGC ACCCTCCCCG GCGGCGAGAG     1200

CGAAGAAGTT GACGTCGACG AGGATGCCTG CACCGGCTGG TACTGCCCCA CGGAACCCAT     1260

TGAATGGGAG CCCCTCCCCA ACGGCTGCCC TGCCGACTTC AGCATCGACC ACCTCCTCCC     1320

CCACGAGAGC GACTGCGGCC AGTATCTACA GTGTGTCCAT GGACAGACTA TCGCAAGACC     1380

TTGCCCTGGA AACCTGCACT TCAGTCCTGC CACACAGTCC TGTGAGTCTC CTGTGACCGC     1440

TGGTTGCCAA GTTTTCGAGT GCGATTCTGA CAACCAGTGC ACATCGACTG CTGCCCCGAC     1500

AGCTGCTCCA ACGGCTGCCC CAACGGCTGC CCCAACGGCT GCCCCAACTG CCGCACCCTC     1560

CACCGTGGTC CCACCTGCAA CGCCACCCGC AACTGCAGCC CCAGTCCCAC CTACAACCGC     1620

AATTCCTACT CCGGCCCCCA CCGCTGCCCC CACCGCAGCT CCTACTACTG CTGCCCCTGA     1680

ATCCCCAACC ACTGTCACAG TACCACCTAC TGCTGCTCCC ACCGCAGCCC CTACTACTGC     1740

TGTCCCTGAA ATCCCAATCA CTGTCACATC AGCGCCTACC GCTGCCCCCA CCGCTGCCCC     1800

CACCGCTGCC CCCACCGCAG CCCCTACTAC TGCTGTCCCA GAAATCCCAA CTACTGTCAC     1860

ATCACCACCT ACTGCTGCCC CCACTACCGC AGCACCTGCC CCAACACCA CAGTCACTGT      1920

ACCACCCACT GCTGCCCCTA CTACCGCAGC ACCTGCTCCC AACACCACAG TGACTGCACC     1980

ACCCACCGCA GCCCCTACTA CCGCAGCACC TGCCCCAAC ACCACAGTCA CTGTACCACC      2040

CACTGCTGCC CCCACTGCAG CTCCCCCTAC CGTCGCACCT GCACCCAACA CCACAGCTGC     2100

CCCGGTAACT ACAACCAGCG CACCAGCTAC CACACCTGAA GATGATGACA TCGACCCCCC     2160

TCTCCCCAAC GACCCCATCA ACCCTTGCGT TGAAGAATGC AACGTTTTGC CCTGGGCTCA     2220

CGCTGACTGC GACAAATACT GGGTCTGTGA CGGCAACAAC CAAGTCCTGG TGGTTTGCTC     2280

TGAGGGTCTC CAGTTCAACC CCACTACTAA GACCTGTGAC TTCGCTTGCA ACGTCGGTTG     2340

CGTGAGGAGC AACATTCAGA TGTCTGAAAG CTACGAAGGA GTCCAGGTCT TCATCCCATG     2400

GAACAAACTA GATGAAGACA TCAGACAGGC GCTGAACTTT GAGTTGTAAA CCTACTTAAA     2460

TTAATGAAGG TTTTGTTTTA TTTTTGAGTT ATTATTCCAA TGGGCGGGAA AGTCCGCCAT     2520

TATTGGGTCT TGCCAGTTTT GAGGAAACCT TTTTTTTTAC TACCAACATT CTTGTGAACC     2580

CATATTTATT ACGTATTAAA CATCGTGATT TGAAAAACGT TACATGATTT TTTCATTAAT     2640

TTGAAACAAT TTATGTTGTT TTTGTTCTCA TTAAATATCA AATATCATTT TCGAAACTGG     2700

CAATTTTGGA TTGAATAAT CAACAAATGG TTAAGAAAAA AACGATTTC TTAAAAATGT       2760

ATTTATTATA AAATGTGTAA ATAAATATAC AAATTAGCAT TTAAAAAAAA AAAAAAAAA      2820

A                                                                    2821
```

(2) INFORMATION FOR SEQ ID NO:3:

(i) SEQUENCE CHARACTERISTICS:
        (A) LENGTH: 786 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Trichoplusia ni
        (F) TISSUE TYPE: peritrophic membrane (xi) SEQUENCE DESCRIPTION: SEQ ID NO:3:

```
Met Ile Lys Thr Leu Leu Phe Leu Thr Ala Leu Gly Leu Val Ala Ala
 1               5                  10                  15

Arg Pro Glu Val Ser Asp Ala Glu Lys Asn Pro Ala Leu His Glu Pro
             20                  25                  30

His Pro Asp Cys Pro Pro Ala Glu Gln His Trp Leu Leu Pro His Glu
         35                  40                  45

Tyr Asp Cys Thr Lys Phe Tyr Tyr Cys Glu Tyr Gly Leu Lys Phe Ile
     50                  55                  60

Ala Pro Arg Asp Cys Ala Pro Gly Thr Glu Phe Lys Phe Ser Ala Gln
65                  70                  75                  80

Thr Cys Val His Ala Ala Leu Ala Gly Cys Thr Leu Pro Gly Pro Pro
                 85                  90                  95

Ala Glu Thr Thr Gln Ala Pro Ala Thr Thr Gln Ala Pro Thr Thr Thr
            100                 105                 110

Gln Ala Pro Thr Thr Thr Gln Ala Pro Thr Thr Thr Gln Ala
        115                 120                 125

Thr Thr Thr Gln Ala Pro Thr Thr Thr Gln Ala Pro Thr Thr Thr
        130                 135                 140

Gln Ala Thr Thr Thr Gln Ala Pro Thr Thr Thr Gln Ala Pro Thr
145                 150                 155                 160

Thr Thr Thr Gln Ala Pro Thr Thr Thr Gln Ala Pro Thr Thr Thr
            165                 170                 175

Gln Ala Pro Thr Thr Thr Gln Ala Pro Thr Thr Thr Gln Ala Pro Thr
            180                 185                 190

Thr Ile Thr Gln Ala Ala Thr Thr Pro Ala Ala Thr Thr Pro Ala Ala
        195                 200                 205

Thr Thr Pro Ala Ala Thr Thr Pro Ala Ala Thr Thr Pro Ala Ala Thr
        210                 215                 220

Thr Pro Gly Val Pro Ala Pro Thr Ser Ala Pro Val Trp Pro Pro Ile
225                 230                 235                 240

Cys Glu Leu Leu Pro Asn Gly Cys Pro Ala Asp Phe Asp Ile His Leu
                245                 250                 255

Leu Ile Pro His Asp Lys Tyr Cys Asn Leu Phe Tyr Gln Cys Ser Asn
            260                 265                 270

Gly Tyr Thr Phe Glu Gln Arg Cys Pro Glu Gly Leu Tyr Phe Asn Pro
        275                 280                 285

Tyr Val Gln Arg Cys Asp Ser Pro Ala Asn Val Glu Cys Asp Gly Glu
        290                 295                 300

Ile Ser Pro Ala Pro Pro Val Thr Glu Gly Asn Glu Asp Glu Asp Ile
305                 310                 315                 320
```

-continued

```
Asp Ile Gly Asp Leu Leu Asp Asn Gly Cys Pro Ala Asn Phe Glu Ile
            325                 330                 335

Asp Trp Leu Leu Pro His Gly Asn Arg Cys Asp Lys Tyr Tyr Gln Cys
            340                 345                 350

Val His Gly Asn Leu Val Glu Arg Arg Cys Gly Ala Gly Thr His Phe
            355                 360                 365

Ser Phe Glu Leu Gln Gln Cys Asp His Ile Glu Leu Val Gly Cys Thr
370                 375                 380

Leu Pro Gly Gly Glu Ser Glu Val Asp Val Asp Glu Asp Ala Cys
385                 390                 395                 400

Thr Gly Trp Tyr Cys Pro Thr Glu Pro Ile Glu Trp Glu Pro Leu Pro
            405                 410                 415

Asn Gly Cys Pro Ala Asp Phe Ser Ile Asp His Leu Leu Pro His Glu
            420                 425                 430

Ser Asp Cys Gly Gln Tyr Leu Gln Cys Val His Gly Gln Thr Ile Ala
            435                 440                 445

Arg Pro Cys Pro Gly Asn Leu His Phe Ser Pro Ala Thr Gln Ser Cys
            450                 455                 460

Glu Ser Pro Val Thr Ala Gly Cys Gln Val Phe Glu Cys Asp Ser Asp
465                 470                 475                 480

Asn Gln Cys Thr Ser Thr Ala Ala Pro Thr Ala Ala Pro Thr Ala Ala
            485                 490                 495

Pro Thr Ala Ala Pro Thr Ala Ala Pro Thr Ala Ala Pro Ser Thr Val
            500                 505                 510

Val Pro Pro Ala Thr Pro Pro Ala Thr Ala Ala Pro Val Pro Pro Thr
            515                 520                 525

Thr Ala Ile Pro Thr Pro Ala Pro Thr Ala Ala Pro Thr Ala Ala Pro
            530                 535                 540

Thr Thr Ala Ala Pro Glu Ser Pro Thr Thr Val Thr Val Pro Pro Thr
545                 550                 555                 560

Ala Ala Pro Thr Ala Ala Pro Thr Thr Ala Val Pro Glu Ile Pro Ile
            565                 570                 575

Thr Val Thr Ser Ala Pro Thr Ala Ala Pro Thr Ala Ala Pro Thr Ala
            580                 585                 590

Ala Pro Thr Ala Ala Pro Thr Thr Ala Val Pro Glu Ile Pro Thr Thr
            595                 600                 605

Val Thr Ser Pro Pro Thr Ala Ala Pro Thr Thr Ala Ala Pro Ala Pro
            610                 615                 620

Asn Thr Thr Val Thr Val Pro Pro Thr Ala Ala Pro Thr Thr Ala Ala
625                 630                 635                 640

Pro Ala Pro Asn Thr Thr Val Thr Val Pro Pro Thr Ala Ala Pro Thr
            645                 650                 655

Ala Ala Pro Pro Thr Val Ala His Ala Pro Asn Thr Thr Ala Ala Pro
            660                 665                 670

Val Thr Thr Thr Ser Ala Pro Ala Thr Thr Pro Glu Asp Asp Asp Ile
            675                 680                 685

Asp Pro Pro Leu Pro Asn Asp Pro Ile Asn Pro Cys Val Glu Glu Cys
            690                 695                 700

Asn Val Leu Pro Trp Ala His Ala Asp Cys Asp Lys Tyr Trp Val Cys
705                 710                 715                 720

Asp Gly Asn Asn Gln Val Leu Val Val Cys Ser Glu Gly Leu Gln Phe
            725                 730                 735
```

```
Asn Pro Thr Thr Lys Thr Cys Asp Phe Ala Cys Asn Val Gly Cys Val
            740                 745                 750

Arg Ser Asn Ile Gln Met Ser Glu Ser Tyr Glu Gly Val Gln Val Phe
            755                 760                 765

Ile Pro Trp Asn Lys Leu Asp Glu Asp Ile Arg Gln Ala Leu Asn Phe
770                 775                 780

Glu Leu
785

(2) INFORMATION FOR SEQ ID NO:4:

(i) SEQUENCE CHARACTERISTICS:
        (A) LENGTH: 805 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Trichoplusia ni
        (F) TISSUE TYPE: peritrophic membrane (xi) SEQUENCE DESCRIPTION: SEQ ID NO:4:

Met Ile Lys Thr Leu Leu Phe Leu Thr Ala Leu Gly Leu Val Ala Ala
1               5                   10                  15

Arg Pro Glu Val Ser Asp Ala Glu Lys Asn Pro Ala Leu His Glu Pro
            20                  25                  30

His Pro Asp Xaa Pro Pro Ala Glu Gln Xaa Xaa Leu Leu Pro Xaa Glu
            35                  40                  45

Tyr Asp Cys Thr Lys Phe Tyr Tyr Cys Glu Tyr Gly Leu Lys Phe Ile
        50                  55                  60

Ala Pro Arg Asp Cys Ala Pro Gly Thr Glu Phe Lys Phe Ser Ala Gln
65              70                  75                  80

Thr Cys Val His Ala Ala Leu Ala Gly Cys Thr Leu Pro Gly Pro Pro
            85                  90                  95

Ala Glu Thr Thr Gln Ala Pro Ala Thr Thr Gln Ala Pro Thr Thr Thr
            100                 105                 110

Gln Ala Pro Thr Thr Thr Gln Ala Pro Thr Thr Thr Gln Ala
            115                 120                 125

Thr Thr Thr Thr Gln Ala Pro Thr Thr Thr Gln Ala Pro Thr Thr Thr
            130                 135                 140

Gln Ala Thr Thr Thr Gln Ala Pro Thr Thr Thr Gln Ala Pro Thr
145                 150                 155                 160

Thr Thr Thr Gln Ala Pro Thr Thr Thr Gln Ala Pro Thr Thr Thr
            165                 170                 175

Gln Ala Pro Thr Thr Thr Gln Ala Pro Thr Thr Thr Gln Ala Pro Thr
            180                 185                 190

Thr Ile Thr Gln Ala Ala Thr Thr Pro Ala Ala Thr Thr Pro Ala Ala
            195                 200                 205

Thr Thr Pro Ala Ala Thr Thr Pro Ala Ala Thr Thr Pro Ala Ala Thr
            210                 215                 220

Thr Pro Gly Val Pro Ala Pro Thr Ser Ala Pro Val Trp Pro Pro Ile
225                 230                 235                 240
```

-continued

```
Cys Glu Leu Leu Pro Asn Gly Cys Pro Ala Asp Phe Asp Ile His Leu
                245                 250                 255

Leu Ile Pro His Asp Lys Tyr Cys Asn Leu Phe Tyr Gln Cys Ser Asn
                260                 265                 270

Gly Tyr Thr Phe Glu Gln Arg Cys Pro Glu Gly Leu Tyr Phe Asn Pro
                275                 280                 285

Tyr Val Gln Arg Cys Asp Ser Pro Ala Asn Val Glu Cys Asp Gly Glu
                290                 295                 300

Ile Ser Pro Ala Pro Pro Val Thr Glu Gly Asn Glu Asp Glu Asp Ile
305                 310                 315                 320

Asp Ile Gly Asp Leu Leu Asp Asn Gly Cys Pro Ala Asn Phe Glu Ile
                325                 330                 335

Asp Trp Leu Pro His Gly Asn Arg Cys Asp Lys Tyr Tyr Gln Cys
                340                 345                 350

Val His Gly Asn Leu Val Glu Arg Arg Cys Gly Ala Gly Thr His Phe
                355                 360                 365

Ser Phe Glu Leu Gln Gln Cys Asp His Ile Glu Leu Val Gly Cys Thr
                370                 375                 380

Leu Pro Gly Gly Glu Ser Glu Val Asp Val Asp Glu Asp Ala Cys
385                 390                 395                 400

Thr Gly Trp Tyr Cys Pro Thr Glu Pro Ile Glu Trp Glu Pro Leu Pro
                405                 410                 415

Asn Gly Cys Pro Ala Asp Phe Ser Ile Asp His Leu Leu Pro His Glu
                420                 425                 430

Ser Asp Cys Gly Gln Tyr Leu Gln Cys Val His Gly Gln Thr Ile Ala
                435                 440                 445

Arg Pro Cys Pro Gly Asn Leu His Phe Ser Pro Ala Thr Gln Ser Cys
                450                 455                 460

Glu Ser Pro Val Thr Ala Gly Cys Gln Val Phe Glu Cys Asp Ser Asp
465                 470                 475                 480

Asn Gln Cys Thr Ser Thr Ala Ala Pro Thr Ala Ala Pro Thr Ala Ala
                485                 490                 495

Pro Thr Ala Ala Pro Thr Ala Ala Pro Thr Ala Ala Pro Ser Thr Val
                500                 505                 510

Val Pro Pro Ala Thr Pro Pro Ala Thr Ala Ala Pro Val Pro Pro Thr
                515                 520                 525

Thr Ala Ile Pro Thr Pro Ala Pro Thr Ala Ala Pro Thr Ala Ala Pro
530                 535                 540

Thr Thr Ala Ala Pro Glu Ser Pro Thr Thr Val Thr Val Pro Pro Thr
545                 550                 555                 560

Ala Ala Pro Thr Ala Ala Pro Thr Thr Ala Val Pro Glu Ile Pro Ile
                565                 570                 575

Thr Val Thr Ser Ala Pro Thr Ala Ala Pro Thr Ala Ala Pro Thr Ala
                580                 585                 590

Ala Pro Thr Ala Ala Pro Thr Thr Ala Val Pro Glu Ile Pro Thr Thr
                595                 600                 605

Val Thr Ser Pro Pro Thr Ala Ala Pro Thr Thr Ala Ala Pro Ala Pro
                610                 615                 620

Asn Thr Thr Val Thr Val Pro Pro Thr Ala Ala Pro Thr Thr Ala Ala
625                 630                 635                 640

Pro Ala Pro Asn Thr Thr Val Thr Ala Pro Pro Thr Ala Ala Pro Thr
                645                 650                 655
```

-continued

```
Thr Ala Ala Pro Ala Pro Asn Thr Thr Val Thr Val Pro Pro Thr Ala
            660         665             670

Ala Pro Thr Ala Ala Pro Pro Thr Val Ala His Ala Pro Asn Thr Thr
            675         680             685

Ala Ala Pro Val Thr Thr Thr Ser Ala Pro Ala Thr Thr Pro Glu Asp
    690             695             700

Asp Asp Ile Asp Pro Pro Leu Pro Asn Asp Pro Ile Asn Pro Cys Val
705             710             715             720

Glu Glu Cys Asn Val Leu Pro Trp Ala His Ala Asp Cys Asp Lys Tyr
            725             730             735

Trp Val Cys Asp Gly Asn Asn Gln Val Leu Val Val Cys Ser Glu Gly
            740             745             750

Leu Gln Phe Asn Pro Thr Thr Lys Thr Cys Asp Phe Ala Cys Asn Val
            755             760             765

Gly Cys Val Arg Ser Asn Ile Gln Met Ser Glu Ser Tyr Glu Gly Val
            770             775             780

Gln Val Phe Ile Pro Trp Asn Lys Leu Asp Glu Asp Ile Arg Gln Ala
785             790             795             800

Leu Asn Phe Glu Leu
                805
```